US011375962B2

(12) United States Patent
Linev

(10) Patent No.: US 11,375,962 B2
(45) Date of Patent: Jul. 5, 2022

(54) FAST FOREIGN OBJECT SCANNER FOR SCANNING HUMAN BODIES

(71) Applicant: ADANI Systems, Inc., Alexandria, VA (US)

(72) Inventor: Vladimir N. Linev, Minsk (BY)

(73) Assignee: Linev Systems, Inc., Alexandria, VA (US)

( * ) Notice: Subject to any disclaimer, the term of this patent is extended or adjusted under 35 U.S.C. 154(b) by 8 days.

(21) Appl. No.: 16/531,339

(22) Filed: Aug. 5, 2019

(65) Prior Publication Data

US 2021/0038175 A1 Feb. 11, 2021

(51) Int. Cl.
*A61B 6/12* (2006.01)
*A61B 6/00* (2006.01)
*G01T 1/163* (2006.01)
*G01T 1/16* (2006.01)

(52) U.S. Cl.
CPC .............. *A61B 6/12* (2013.01); *A61B 6/4441* (2013.01); *A61B 6/505* (2013.01); *A61B 6/5235* (2013.01); *G01T 1/163* (2013.01); *A61B 6/4241* (2013.01); *A61B 6/482* (2013.01); *G01T 1/16* (2013.01)

(58) Field of Classification Search
CPC ......... A61B 6/12; A61B 6/4441; A61B 6/505; G01V 5/0066; G01V 5/0005; G01T 1/16
See application file for complete search history.

(56) References Cited

U.S. PATENT DOCUMENTS

| | | | | |
|---|---|---|---|---|
| 3,784,820 | A * | 1/1974 | Miraldi | G01T 1/1642 250/362 |
| 4,230,129 | A * | 10/1980 | LeVeen | A61B 6/12 378/65 |
| 5,287,546 | A * | 2/1994 | Tesic | A61B 6/505 600/407 |
| 5,464,984 | A * | 11/1995 | Cox | G01T 1/2018 348/E3.018 |
| 5,509,042 | A * | 4/1996 | Mazess | A61B 6/463 378/54 |
| 5,657,369 | A * | 8/1997 | Stein | G21K 1/10 378/208 |
| 5,715,820 | A * | 2/1998 | Stein | A61B 6/482 378/146 |
| 5,745,544 | A * | 4/1998 | Mazess | A61B 6/505 378/54 |
| 5,748,705 | A * | 5/1998 | Stein | A61B 6/488 378/54 |
| 6,147,352 | A * | 11/2000 | Ashburn | A61B 6/037 250/363.08 |

(Continued)

*Primary Examiner* — Dani Fox
*Assistant Examiner* — Soorena Kefayati
(74) *Attorney, Agent, or Firm* — Bardmesser Law Group

(57) ABSTRACT

An X-ray imaging system includes a frame; a gantry mounted on the frame; an electromagnetic linear drive coupled to the gantry for translating the gantry in a horizontal direction; a C-arm mounted on the gantry, the C-arm rotatable across at least a 90 degree angle; an X-ray source mounted to one end of C-arm; an X-ray detector array mounted to the opposite end of the C-arm. The array is formed of a plurality of array elements, each array element formed of a plurality of linear detectors. Each array element is mounted perpendicular to a radial line between a focal spot of the X-ray source and a middle of each array element, and the X-ray detector array has a focal point at the X-ray source.

19 Claims, 24 Drawing Sheets

(56) References Cited

U.S. PATENT DOCUMENTS

| Patent/Pub No. | Date | Inventor | Classification |
|---|---|---|---|
| 6,217,214 B1* | 4/2001 | Cabral | A61B 6/505 378/208 |
| 6,256,374 B1* | 7/2001 | Tomasetti | A61B 6/464 378/98.2 |
| 6,438,201 B1* | 8/2002 | Mazess | A61B 6/405 378/108 |
| 6,940,941 B2* | 9/2005 | Gregerson | A61B 6/4411 378/197 |
| 7,903,779 B2* | 3/2011 | Gregerson | G06T 11/005 378/4 |
| 8,424,133 B1* | 4/2013 | Rossi | A61B 6/0442 5/607 |
| 2001/0048732 A1* | 12/2001 | Wilson | A61B 6/4233 378/54 |
| 2002/0018542 A1* | 2/2002 | Fenkart | G01N 23/046 378/57 |
| 2004/0022350 A1* | 2/2004 | Gregerson | A61B 6/4405 378/15 |
| 2005/0117700 A1* | 6/2005 | Peschmann | G01V 5/00 378/57 |
| 2005/0234327 A1* | 10/2005 | Saracen | A61B 6/4458 600/407 |
| 2006/0291623 A1* | 12/2006 | Smith | G01N 23/20 378/69 |
| 2007/0085011 A1* | 4/2007 | Ritter | A61B 6/5235 250/363.05 |
| 2008/0082002 A1* | 4/2008 | Wilson | A61B 5/7275 378/54 |
| 2009/0086907 A1* | 4/2009 | Smith | G01V 5/0066 378/57 |
| 2009/0147925 A1* | 6/2009 | De Villiers | A61B 6/032 378/207 |
| 2009/0296880 A1* | 12/2009 | Beets | A61B 6/4441 378/98.12 |
| 2011/0058649 A1* | 3/2011 | Wear | A61B 6/505 257/E31.015 |
| 2011/0085640 A1* | 4/2011 | Fadler | A61B 6/4441 378/65 |
| 2011/0122990 A1* | 5/2011 | Dafni | A61B 6/032 378/4 |
| 2011/0182402 A1* | 7/2011 | Partain | A61B 6/587 378/9 |
| 2011/0280379 A1* | 11/2011 | Maschke | A61B 6/4458 901/15 |
| 2012/0014503 A1* | 1/2012 | Ullberg | A61B 6/5205 378/19 |
| 2012/0087465 A1* | 4/2012 | Ikhlef | A61B 6/00 378/19 |
| 2012/0232375 A1* | 9/2012 | Zebaze | A61B 6/032 600/407 |
| 2013/0039472 A1* | 2/2013 | Morton | G01V 5/0025 378/88 |
| 2013/0235971 A1* | 9/2013 | Oreper | G01T 1/2985 378/57 |
| 2013/0343519 A1* | 12/2013 | Ma | A61B 6/542 378/54 |
| 2014/0171725 A1* | 6/2014 | Adler | G21F 3/00 600/1 |
| 2014/0211925 A1* | 7/2014 | Dong | A61B 6/583 378/207 |
| 2014/0226789 A1* | 8/2014 | Bendahan | G01V 5/0041 378/86 |
| 2015/0146853 A1* | 5/2015 | Spartiotis | A61B 6/547 378/62 |
| 2015/0246244 A1* | 9/2015 | Sossong | A61B 6/4266 600/427 |
| 2015/0366519 A1* | 12/2015 | Furuta | G01T 1/2985 600/431 |
| 2016/0203598 A1* | 7/2016 | Nakaya | G06T 7/11 382/132 |
| 2017/0053414 A1* | 2/2017 | Flohr | G06T 11/005 |
| 2017/0245826 A1* | 8/2017 | Kasaoka | A61B 6/4452 |
| 2017/0258425 A1* | 9/2017 | Risher-Kelly | A61B 6/4441 |
| 2017/0293039 A1* | 10/2017 | Blenk | A61B 6/102 |
| 2017/0340268 A1* | 11/2017 | Danielsson | A61B 5/4561 |
| 2018/0192967 A1* | 7/2018 | Koehler | A61B 6/4233 |
| 2018/0240842 A1* | 8/2018 | Meylan | A61B 6/4241 |
| 2018/0289339 A1* | 10/2018 | Fortuna | A61B 6/4241 |
| 2018/0304098 A1* | 10/2018 | Humber | A61B 6/035 |
| 2018/0356352 A1* | 12/2018 | Pipino | G01N 23/083 |
| 2019/0179040 A1* | 6/2019 | Luu | G01T 1/2985 |
| 2019/0223278 A1* | 7/2019 | Jordan | A61B 6/5264 |
| 2019/0388044 A1* | 12/2019 | Hirose | A61B 6/487 |
| 2020/0029927 A1* | 1/2020 | Wilson | A61B 5/0077 |
| 2020/0060638 A1* | 2/2020 | Assolari | A61B 6/4476 |
| 2020/0163643 A1* | 5/2020 | Desaute | A61B 6/4233 |
| 2020/0205763 A1* | 7/2020 | Helm | G01N 23/04 |

* cited by examiner

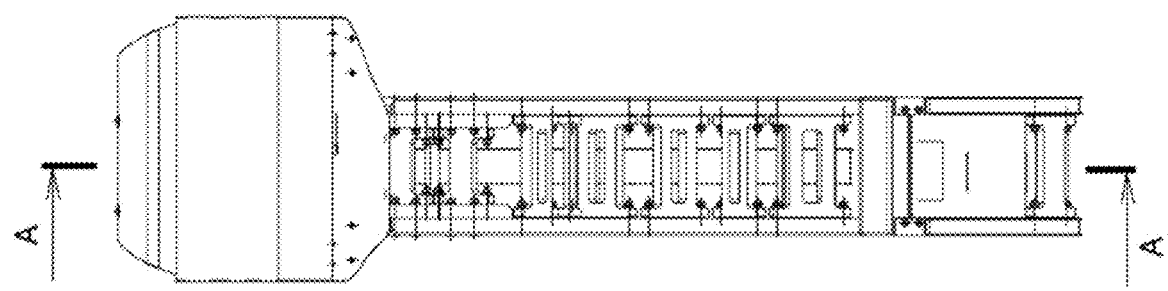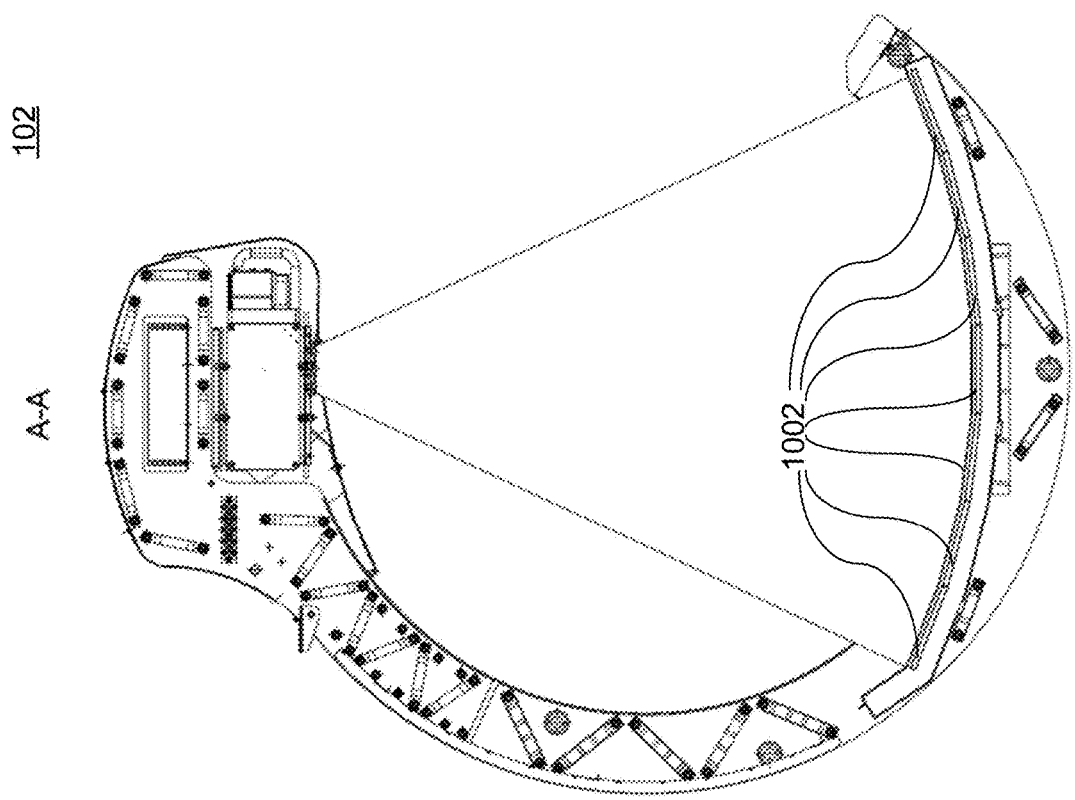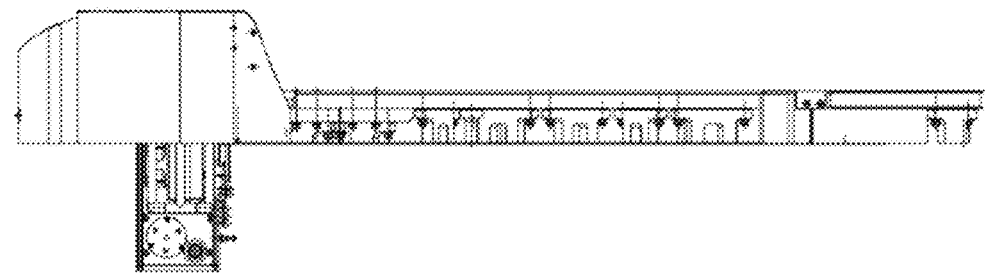
FIG. 10

FAST FOREIGN OBJECT SCANNER FOR SCANNING HUMAN BODIES

BACKGROUND OF THE INVENTION

Field of the Invention

The present invention relates to a scanner for human bodies, particularly a scanner for foreign objects, such as a scanner used in forensic applications.

Description of the Related Art

Conventional scanners, such as those exemplified by U.S. Pat. No. 7,873,142 B2, suffer from a problem of fast overheating of X-Ray source and interruption of the scanning process for its cooling, and, as a consequence, relatively low throughput.

The use of X-ray radiation sources with high parameters of the anode current up to 400 mA has several main challenges:
- fast heating of the x-ray tube, which limits the scanning time to 13-15 seconds;
- a long period of time of inactivity between the scan to cool the x-ray tube;
- the low period of the lifetime of the x-ray tube and the high cost of replacing it.

Accordingly, there is a need in the art for a forensic foreign object scanner that addresses these problems.

SUMMARY OF THE INVENTION

The invention relates to a fast forensic foreign object scanner that substantially overcomes one or more disadvantages of the related art.

In an exemplary embodiment, the use of a new combination of a low-current X-ray source up to 2.5 mA and a detector with TDS technology makes it possible to obtain continuously high-quality X-ray photographs without limiting the scanning time and without forced inactivity to cool the X-ray source.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED FIGURES

The accompanying drawings, which are included to provide a further understanding of the invention and are incorporated in and constitute a part of this specification, illustrate embodiments of the invention and together with the description serve to explain the principles of the invention.

In the drawings:

FIG. 10 is a different side view of C-frame (C-arm).

DETAILED DESCRIPTION OF THE PREFERRED EMBODIMENTS

Reference will now be made in detail to the preferred embodiments of the present invention, examples of which are illustrated in the accompanying drawings.

Figure 1:
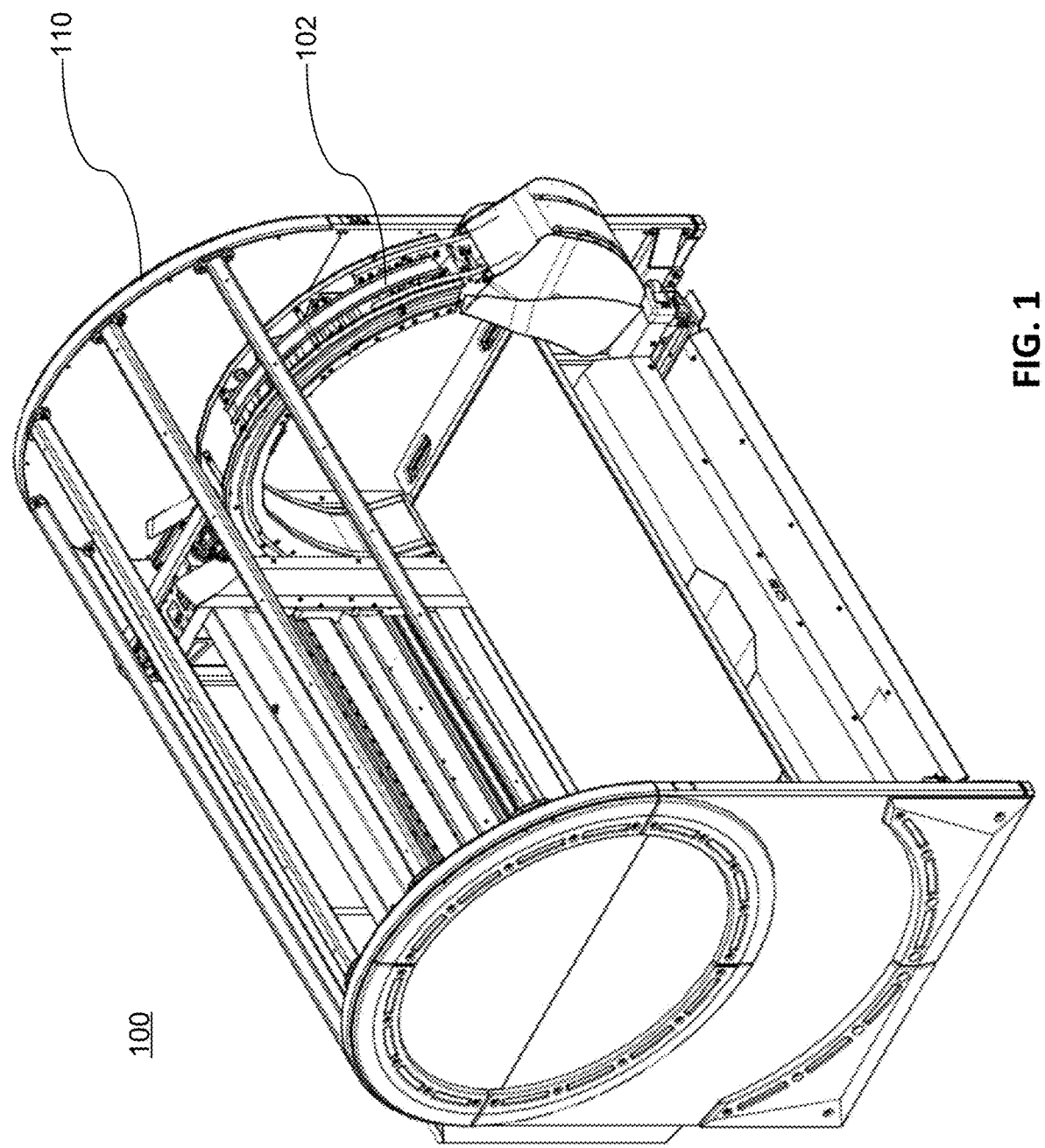
FIG. 1 is a perspective three-dimensional view of the foreign object scanner of the present invention.
Figure 2:
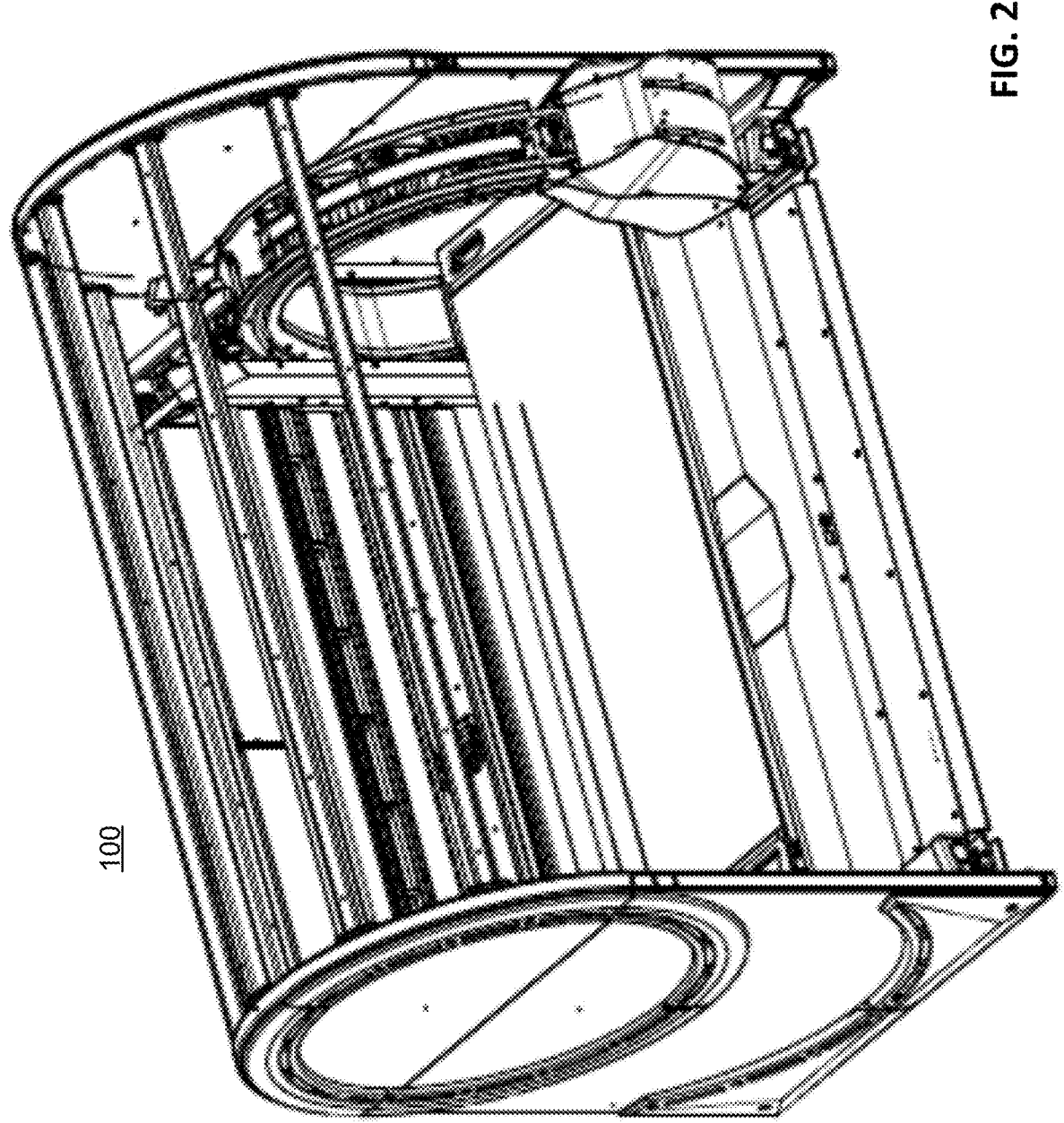
FIG. 2 is another perspective three-dimensional view of the foreign object scanner of the present invention.
Figure 3:
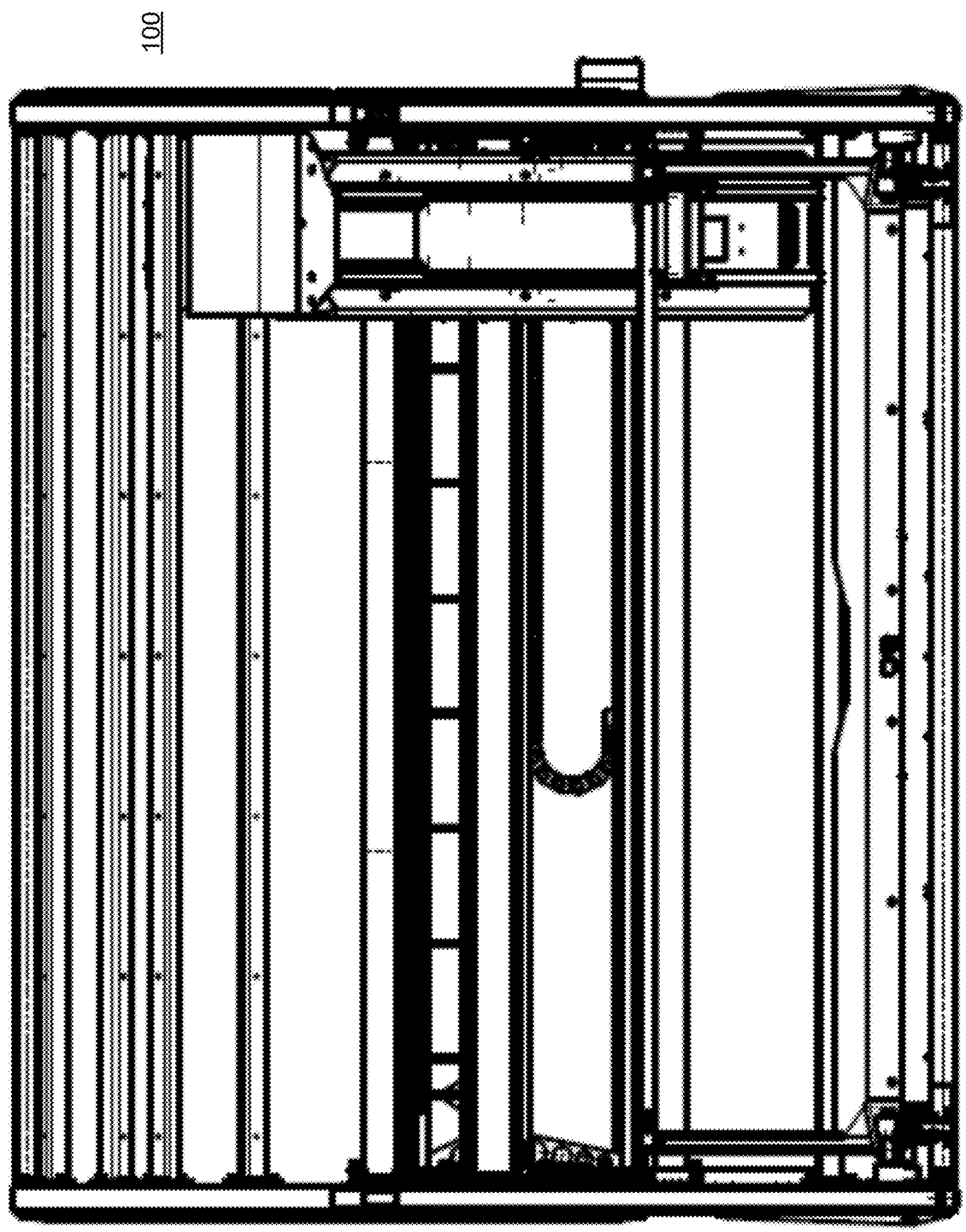
FIG. 3 is a side view of the foreign object scanner of the present invention.
Figure 4:
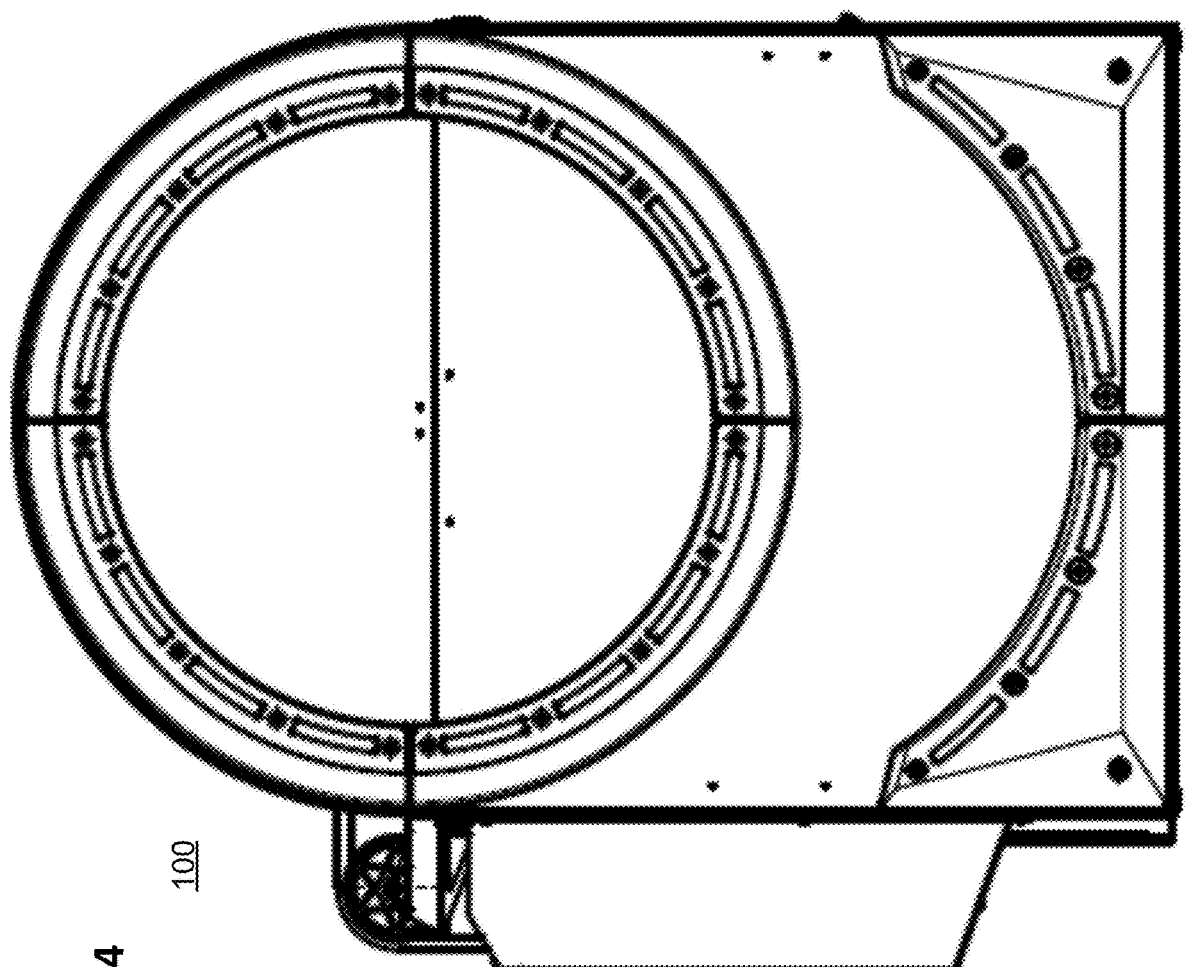
FIG. 4 is a different side view of the foreign object scanner of the present invention.
Figure 5:
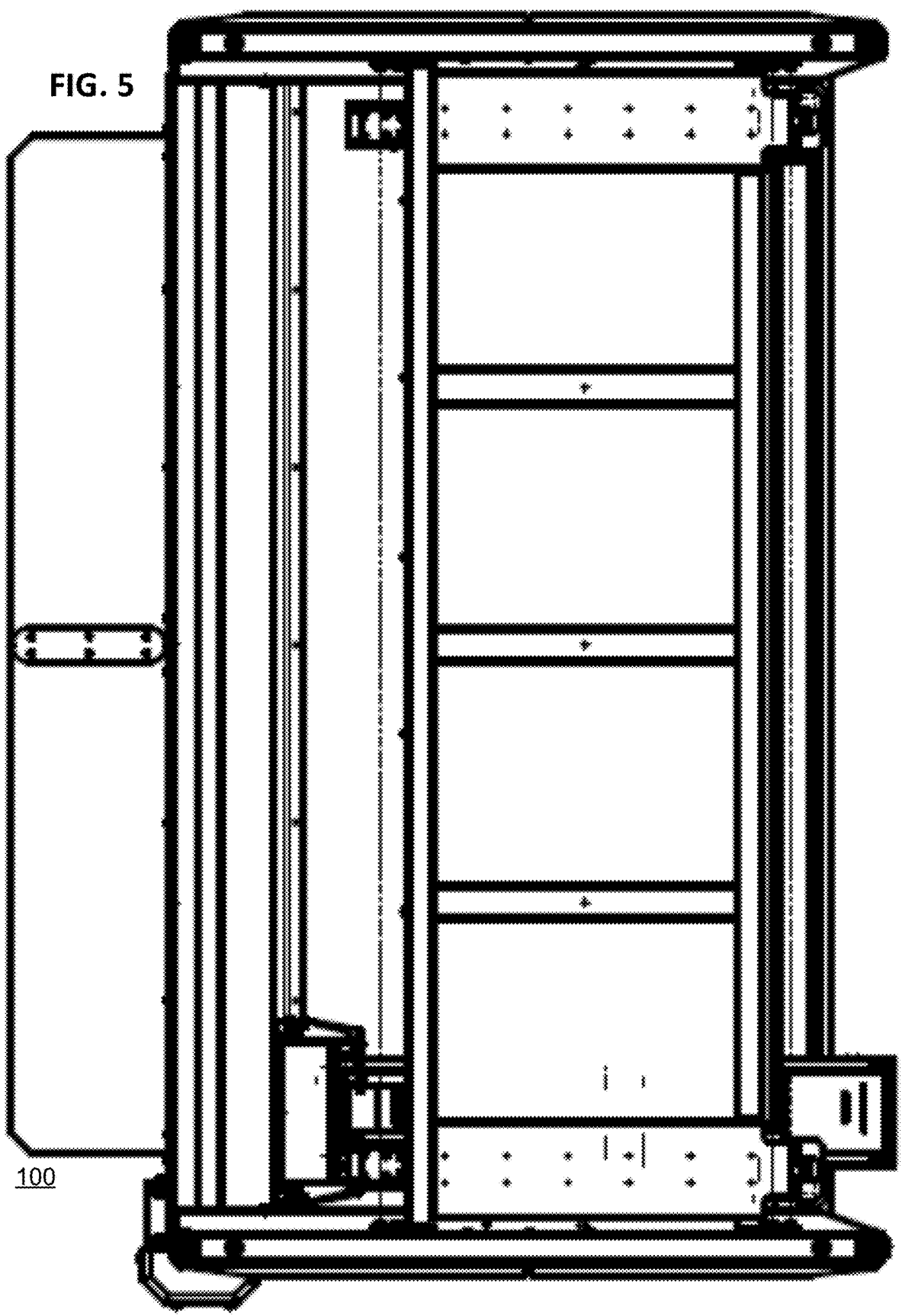
FIG. 5 is a top view of the foreign object scanner of the present invention.

In order to solve the problem of generating a high-contrast image of the entire human body in a rapid manner, the following combination of elements is utilized for a scanner 100 (see FIG. 1).

Figure 6:
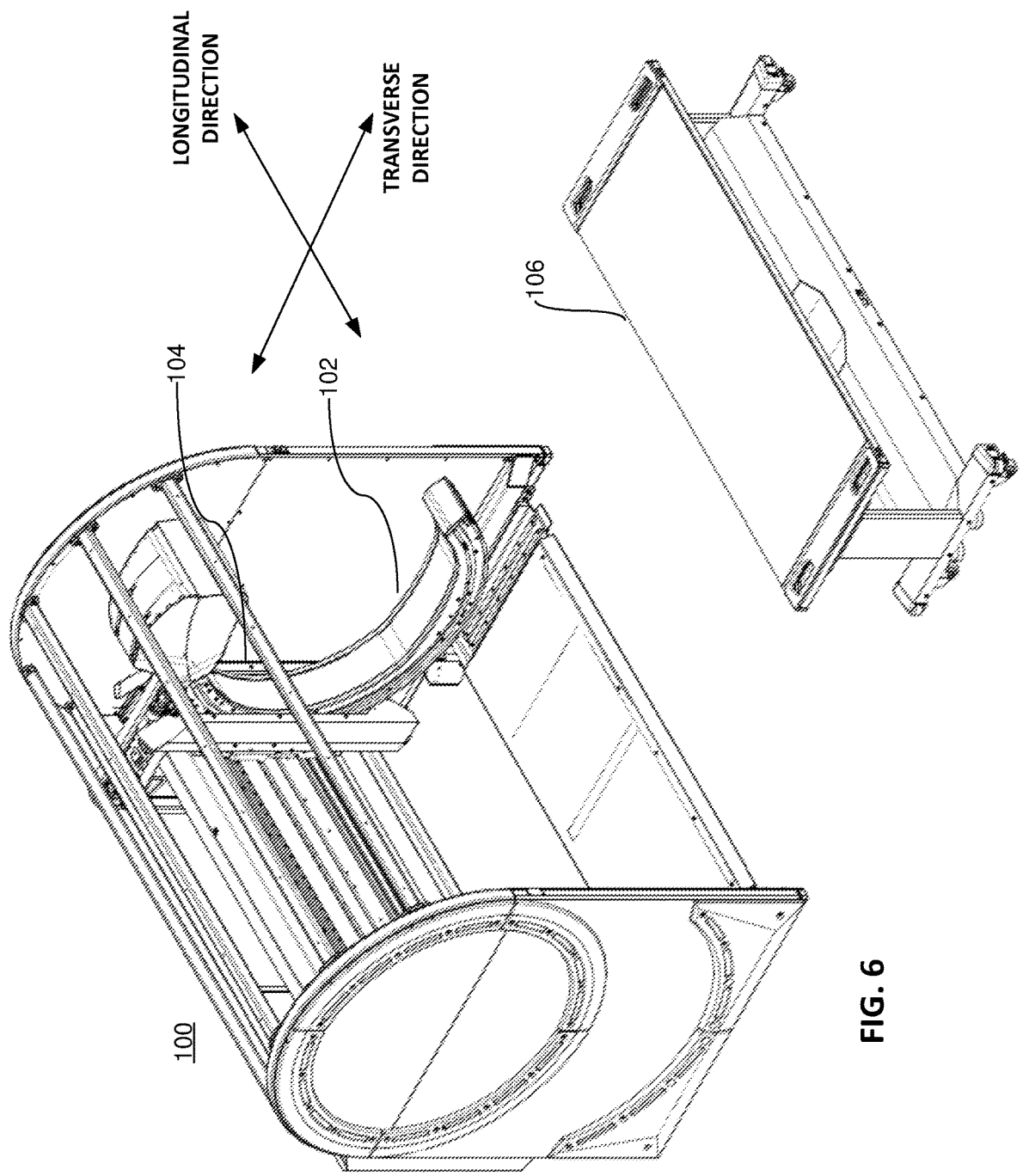
FIG. 6 is a perspective three-dimensional view of the foreign object scanner of the present invention with the table out.
Figure 7:
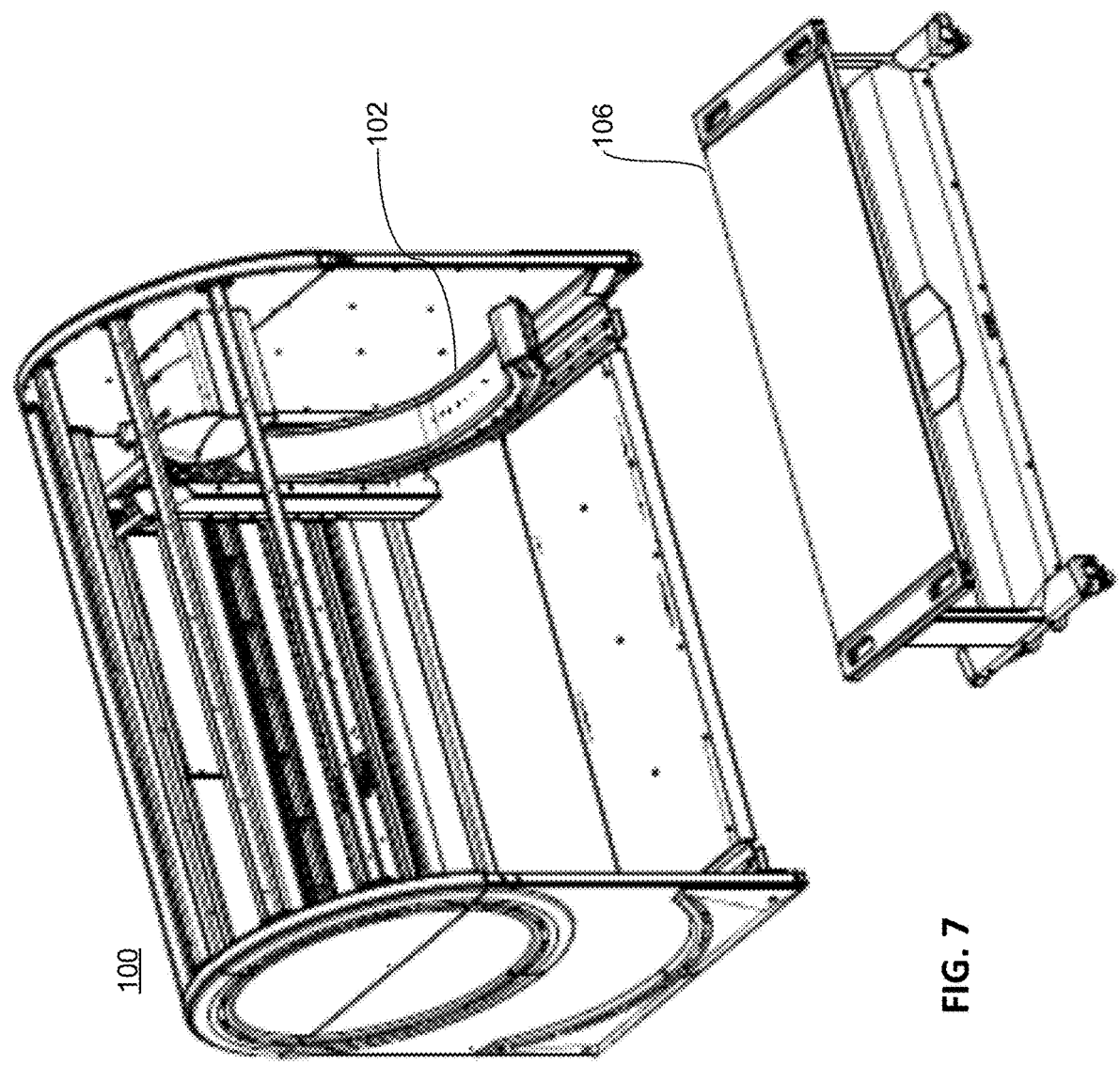
FIG. 7 is another perspective three-dimensional view of the foreign object scanner of the present invention with the table out.
Figure 14:
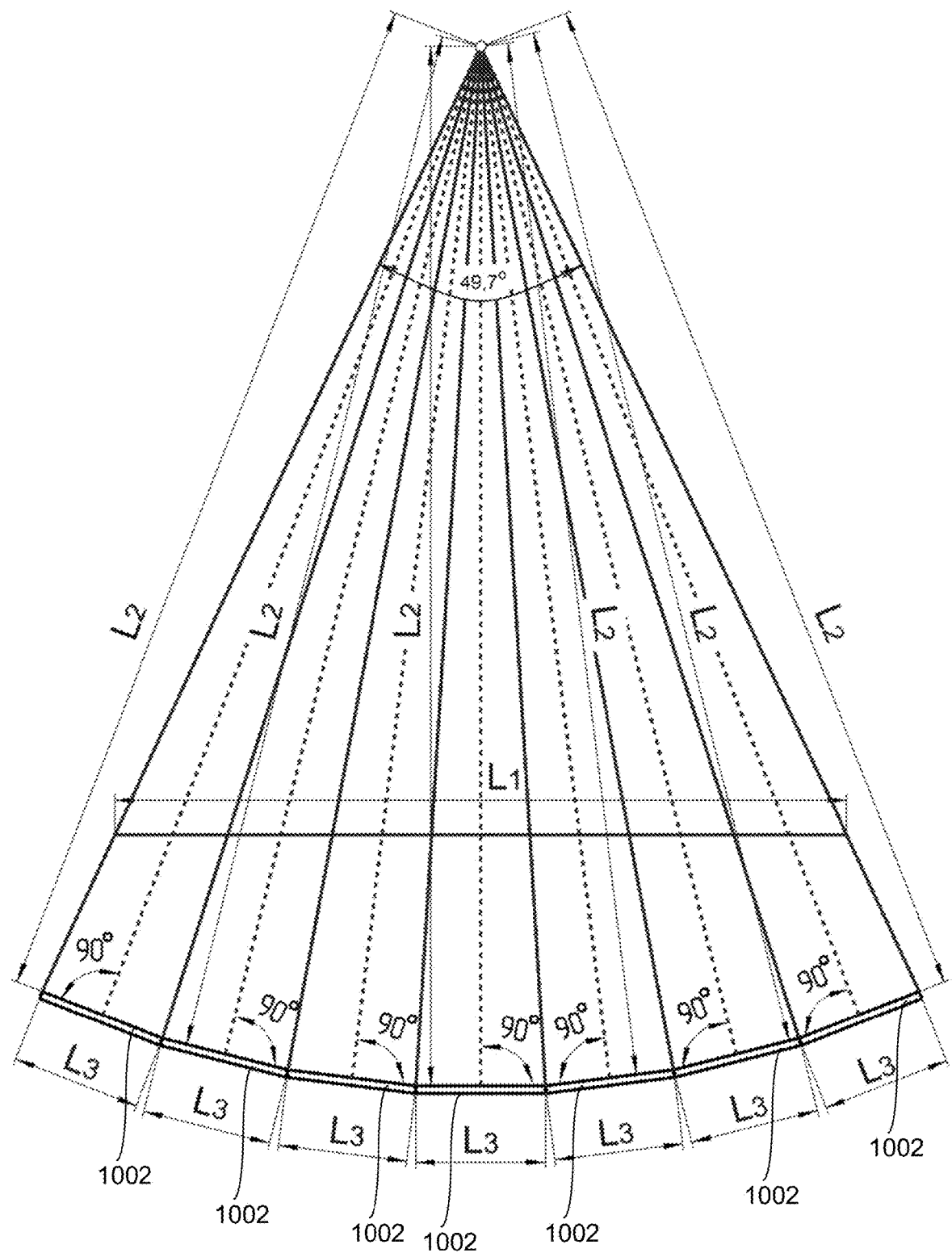
FIG. 14 is a layout of detector boards on the C-frame.
Figure 15:
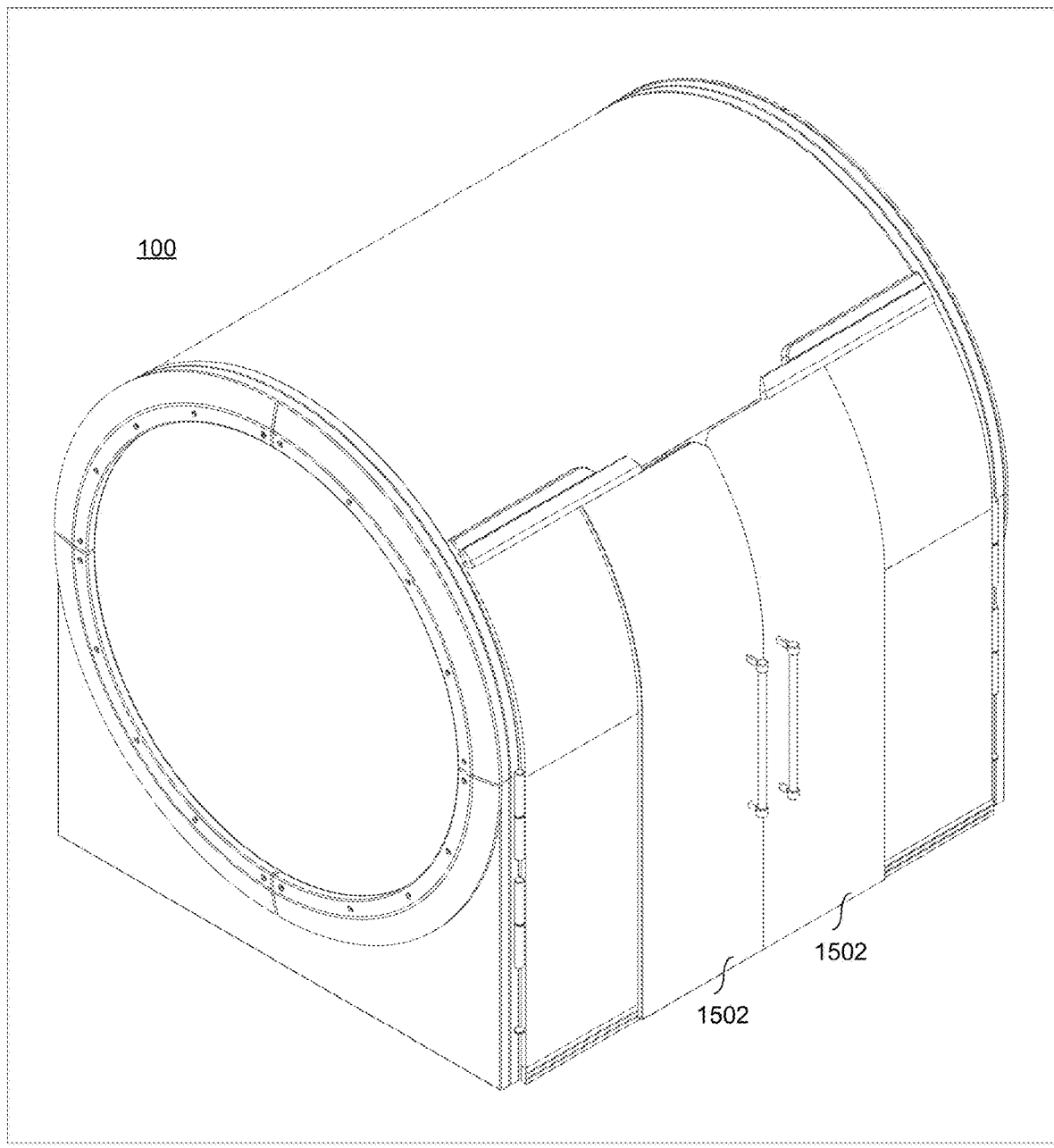
FIG. 15-FIG. 20 show perspective views of a variation of the design with sliding doors.
Figure 16:
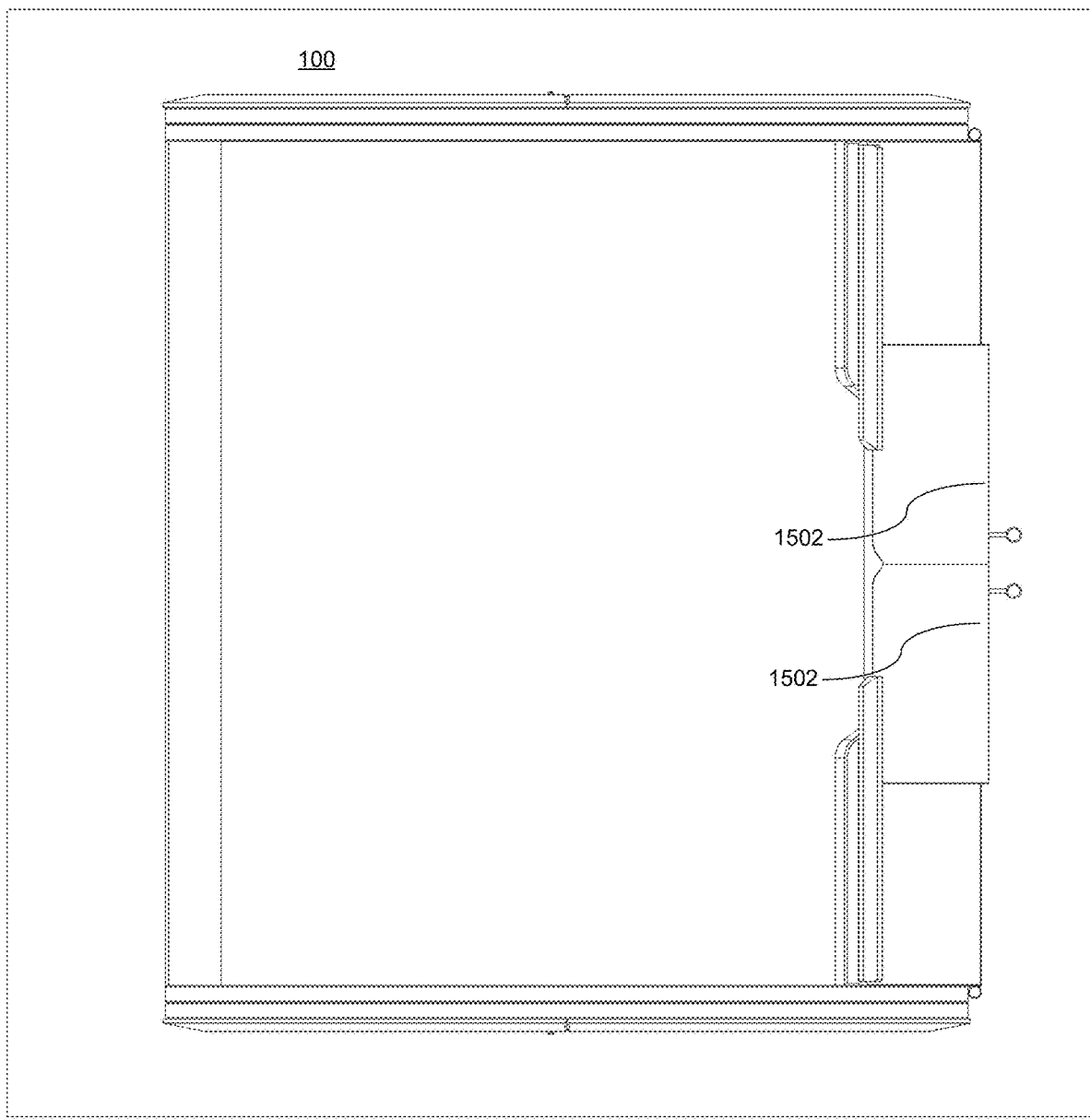
Figure 17:
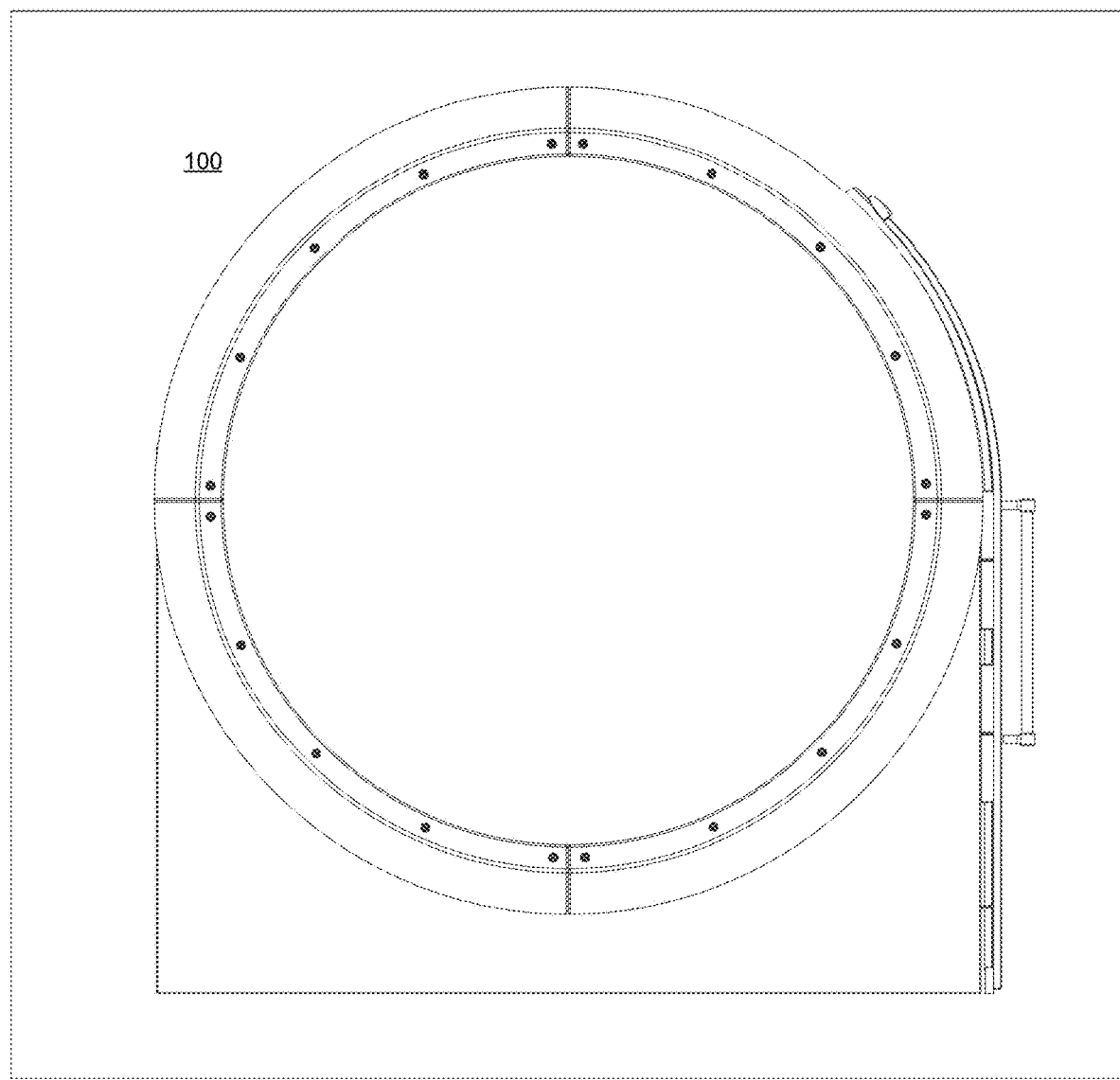
Figure 18:
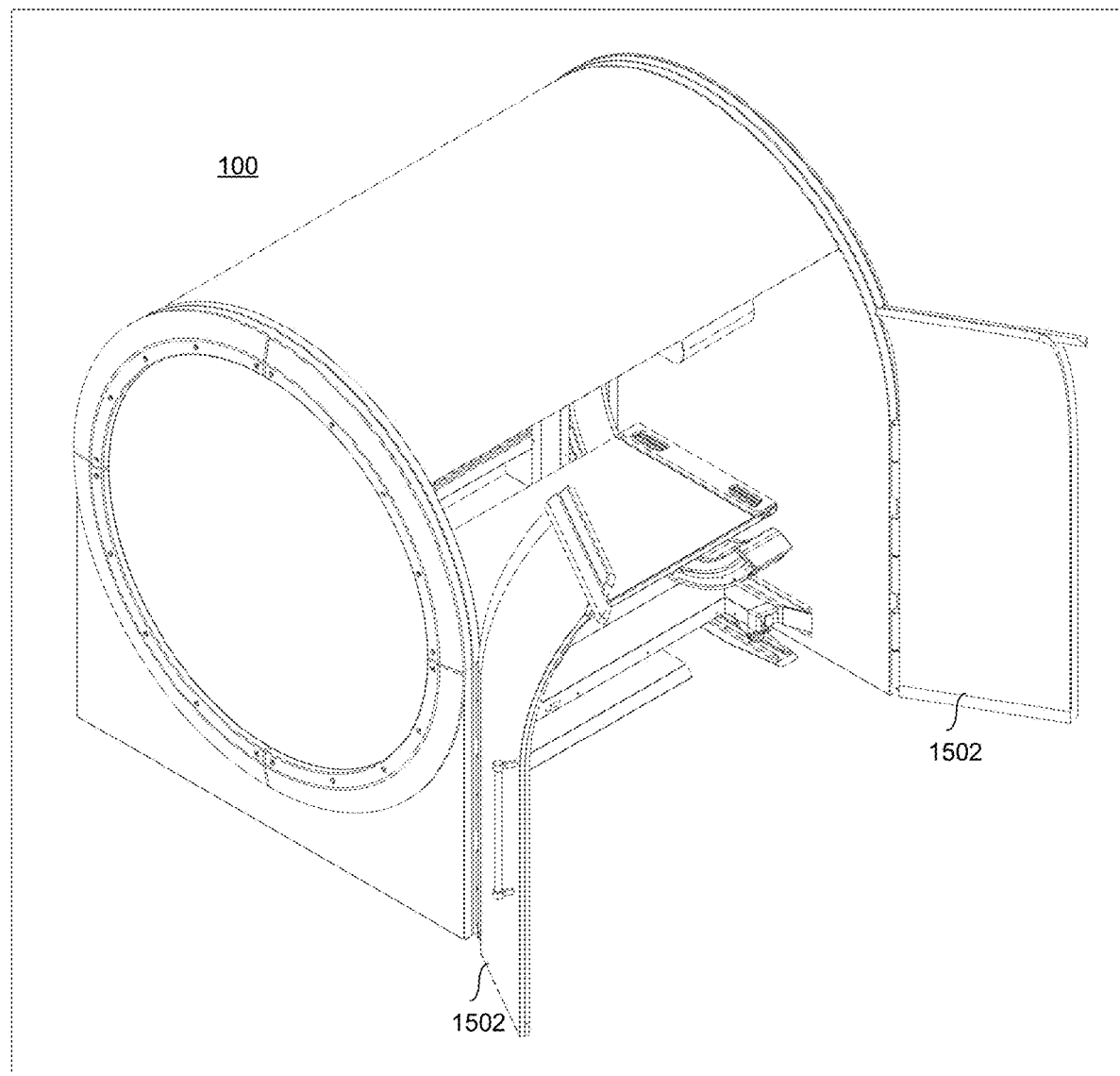
Figure 19:
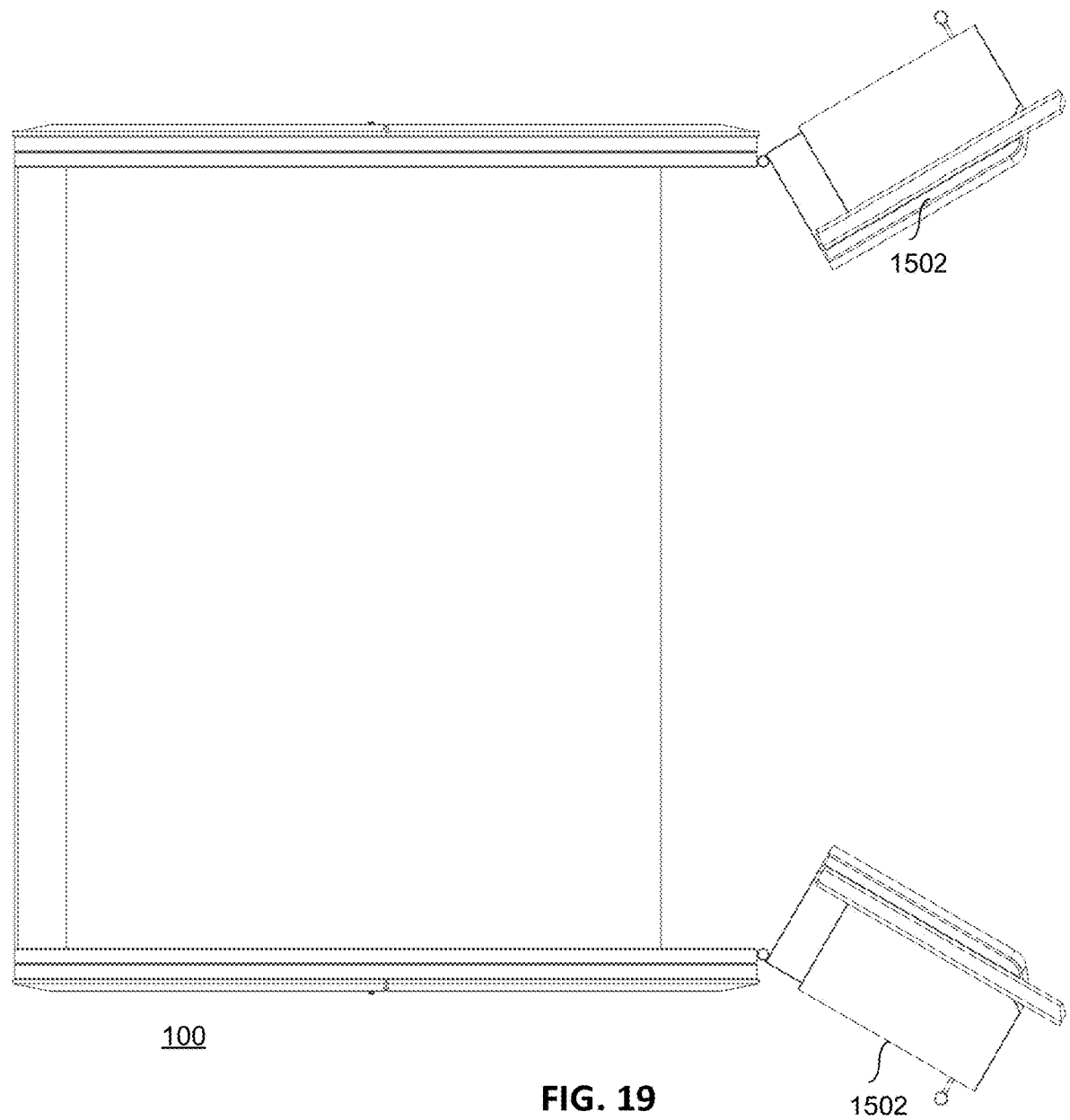
Figure 20:
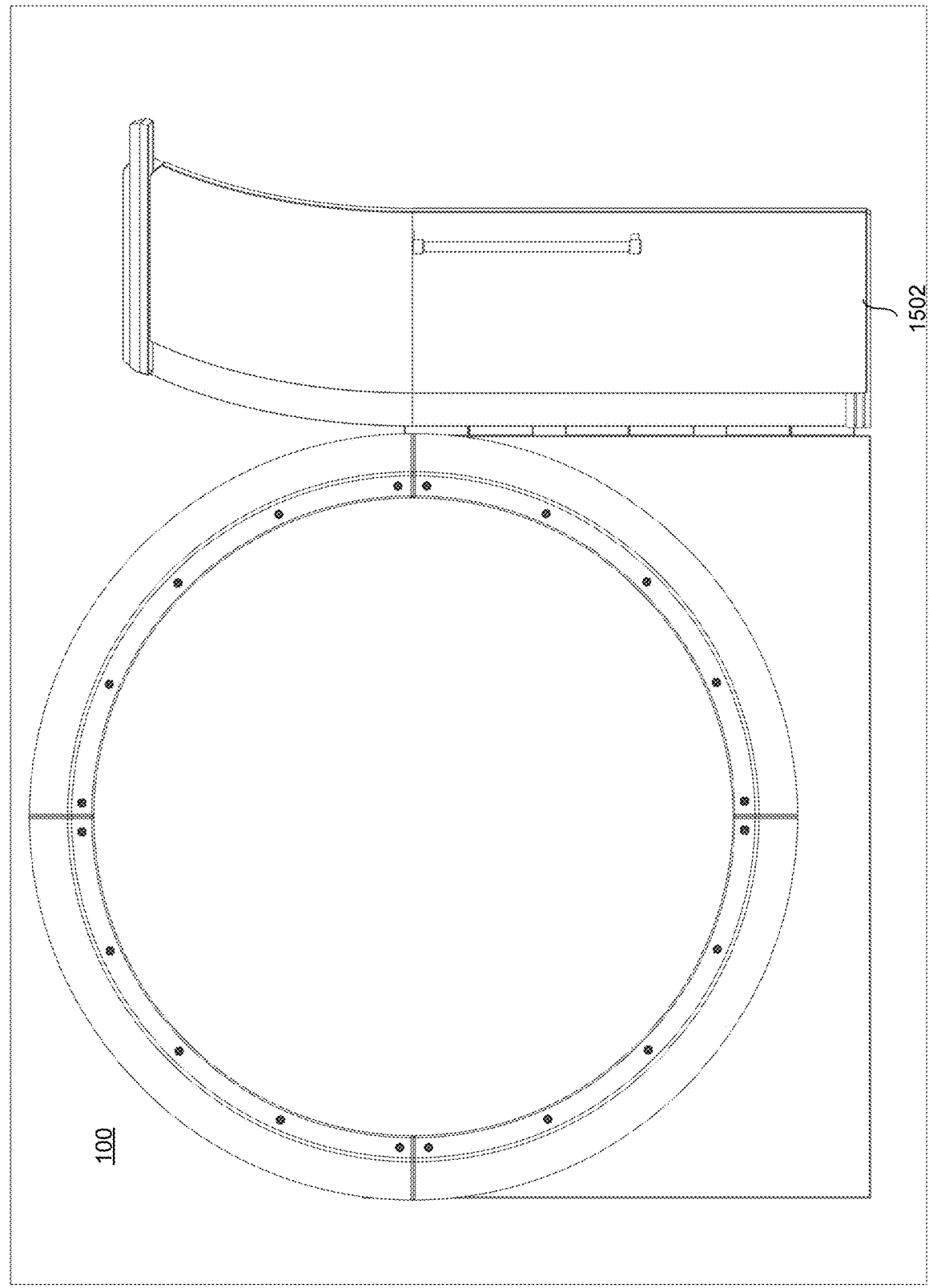

A set of detector arrays 1002 (see FIGS. 10 and 14) are located on the C-frame 102 (see FIG. 6) (which is itself mounted on a gantry 104, see FIG. 1), at the same radius from a focal point of the X-ray source. In the particular example, the radius is 1237.6 mm, although, obviously, the particular radius depends on engineering design considerations. In the exemplary embodiment, the active length of each detector array is 153.6 mm and the active width of each detector array is 6.4 mm Each detector array has 64 pixel lines and the size of each pixel is 0.1×0.1 mm. A total of 7 detector arrays are used in this example. The radius line is perpendicular to the center of each detector array 1002 (see FIG. 14). The width of the table 106 (see FIG. 1) that is transparent to the X-rays is 830 mm, in the exemplary embodiment.

Such an arrangement of the detector arrays 1002 permits to (1) considerably increase the width of the transparent portion of the table 106 (i.e., the width of the object/body being scanned), while keeping the overall dimensions of the scanner to a minimum; and (2) to generate an image of the object with minimal geometric distortions, which, in turn, permits to (3) use algorithms for generating a high-contrast image.

Figure 8:
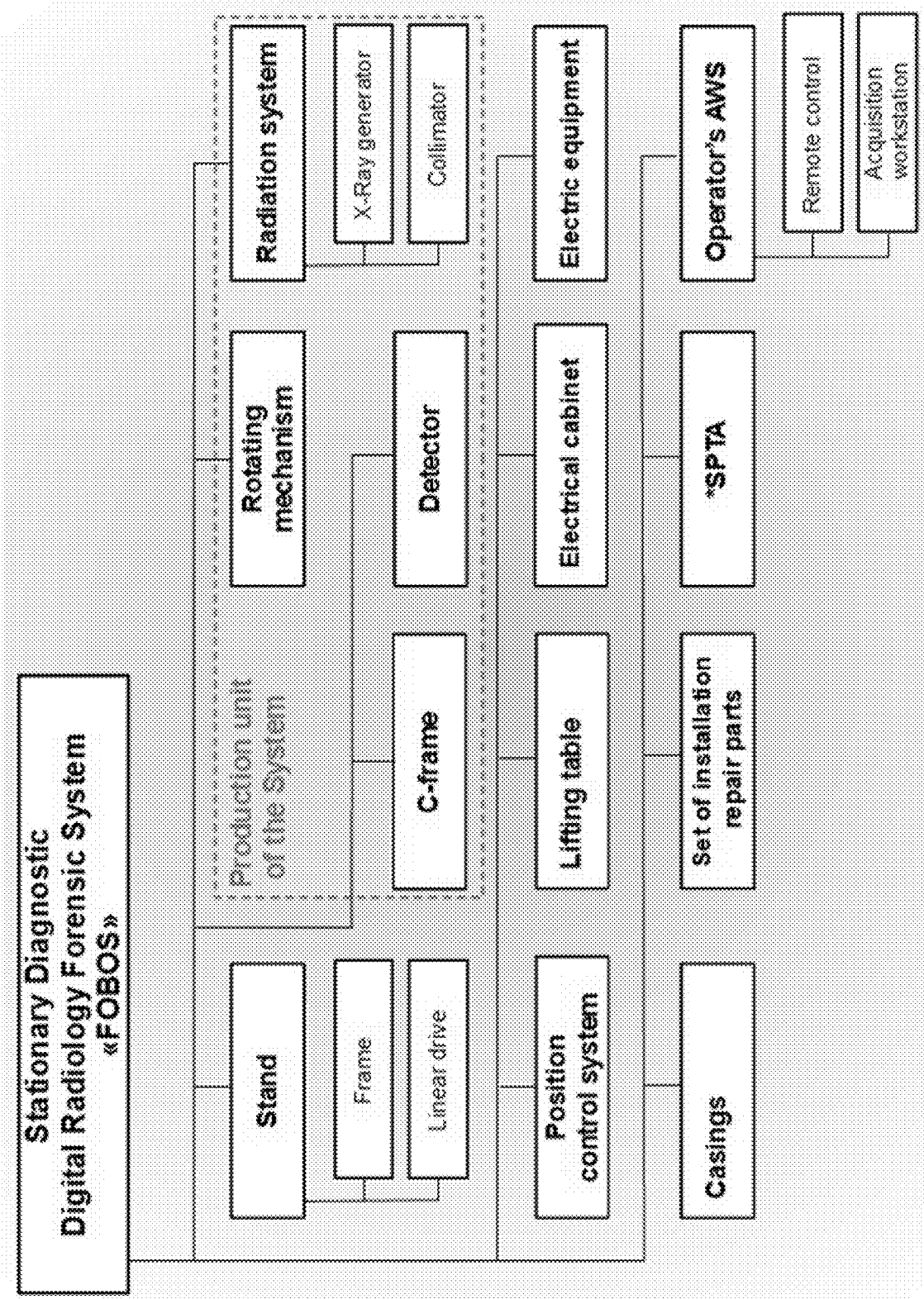
FIG. 8 is a system block diagram of the system.

The scanner system includes the following components (see system block diagram in FIG. 8):
The stand includes:
Frame 110;
Linear drive;
Rotating mechanism;
C-frame 102;
Detector (see elements 1002 in FIGS. 10 and 14);
Radiation system composed of:
X-Ray generator 902 (see FIG. 9);
Collimator;
Position control system;
Lifting table;
Electrical cabinet;
Electric equipment;
Casings;
Operator's AWS composed of:
Remote control;
Acquisition workstation.

The rotating mechanism, C-frame, detector and radiation system form a production unit of the system.

The use of the selected parameters of the X-ray generator and the detector arrays permit (1) a continuous imaging process that does not require interruptions for cooling of the X-ray source, (2) using TDS technology. The image is processed using a computer, where it is possible to adjust multi-threaded distributed computing using capabilities of a multi-core processor. A 2D digital image is formed so that the number of elements (pixels) along one coordinate (in the scanning direction) is determined by the number of scanning steps (number of counting) and the number of detectors in the direction perpendicular to the scanning direction along the other coordinate. For high speed data processing from the detector and image generation, a personal computer with a processor INTEL CORE i7-8700 or better may be used. Moreover, it is possible to programmatically adjust the priority of distributed computing using the capabilities of multi-thread multi-core computing. This allows to evenly use the computational capabilities of the processor, making the calculation process more productive and reliable.

The detector receives X-rays and generates images in TDS (Time Delayed Summation) mode. This is when an object moves across the detector in such a way the same area is imaged by each row of the detector at a time allowing each row to be summed to get a more statistically accurate sample of that section of the object. These samples form lines in the output image and so form a complete scan of the object.

In TDS mode, detector pixel values are shifted along rows during image acquisition to compensate for detector motion. This detector is a non-scintillating detector type (e.g., cadmium-telluride) to directly count the photons.

This detector allows to generate good quality X-Ray image using relatively low-current X-ray sources, e.g., up to 2.5 mA current requirements for the X-ray source. Compare this with conventional scanners that use scintillator-type detectors, and require a source that has a max current of 400 mA—which means it can only work in this regime only 13-15 sec, and then requires to be off-line for cooling. This, in turn, forces the source to move at high speed, relative to the object being scanned. The present scanner does not need such high speed because doesn't need cooling after each scanning (in the exemplary embodiment, the scanner has an X-ray source with max. current of 2.5 mA, 200 kV, focal spot 0.8 mm, fan angle of 49.7°, see FIG. 14, in one example).

Figure 13:
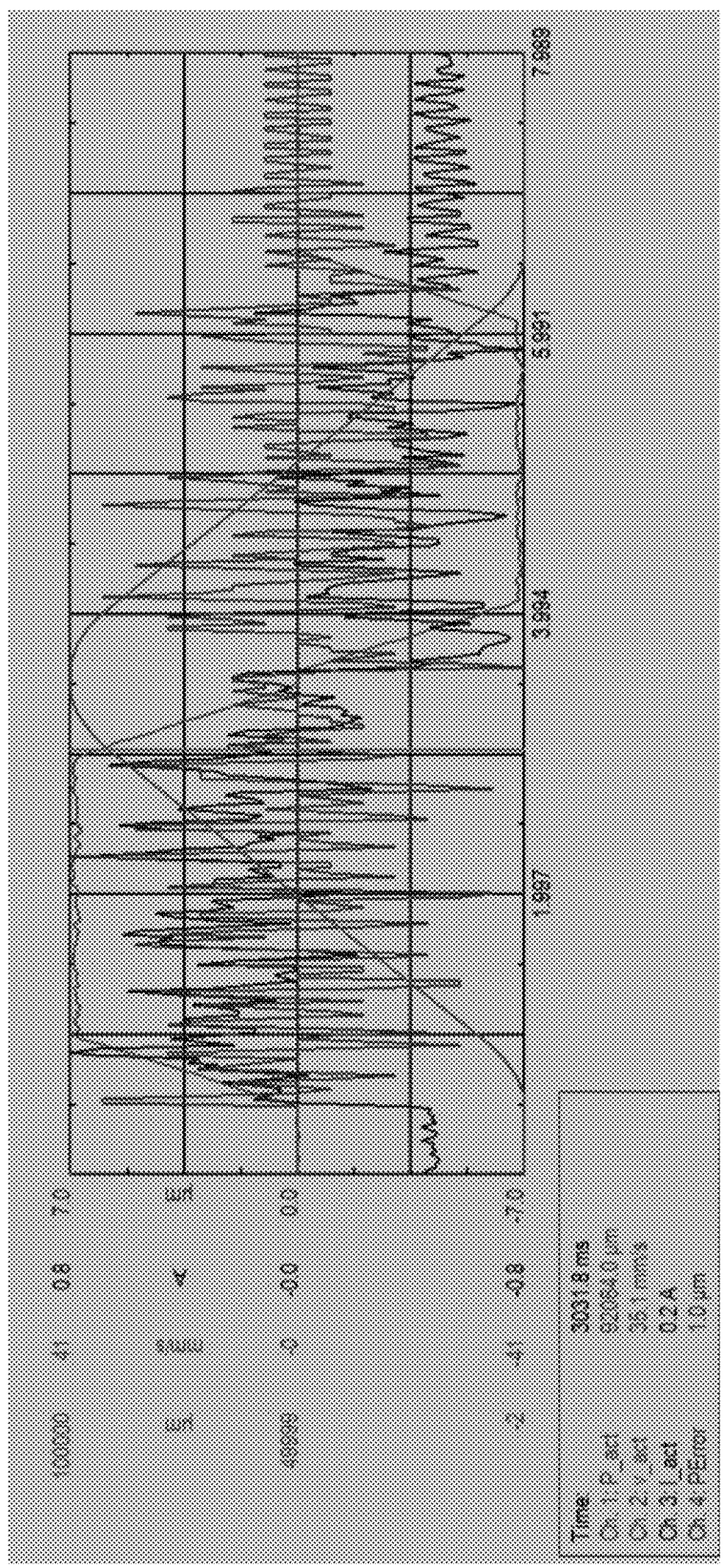
FIG. 13 is a positioning precision of the electromagnetic drive.

The use of an electromagnetic drive permits high-precision in positioning of the C-frame (and of the detector arrays), while the movement of the C-frame is relatively smooth in the lateral direction (the amplitude of the vibrations is less than 50 microns, which again assists in generating a high-quality high-contrast image). The electromagnetic drive is a linear synchronous motor that includes a moving element (anchor) and a magnetic strip (stator). The anchor has a magnetic geared drive that fits into the windings, which is sealed with a thermally conductive compound. The stator includes rare earth magnets of alternating polarity. A typical gap between the anchor and the stator is about 1 mm High positioning precision (see FIG. 13, where positioning precision is about 7 microns) is enabled by the fact that no mechanical coupling is needed—this permits high precision of the motor, high reliability, highly stable electromotive force, accurate and high acceleration, and very precise movement and positioning.

Figure 9:
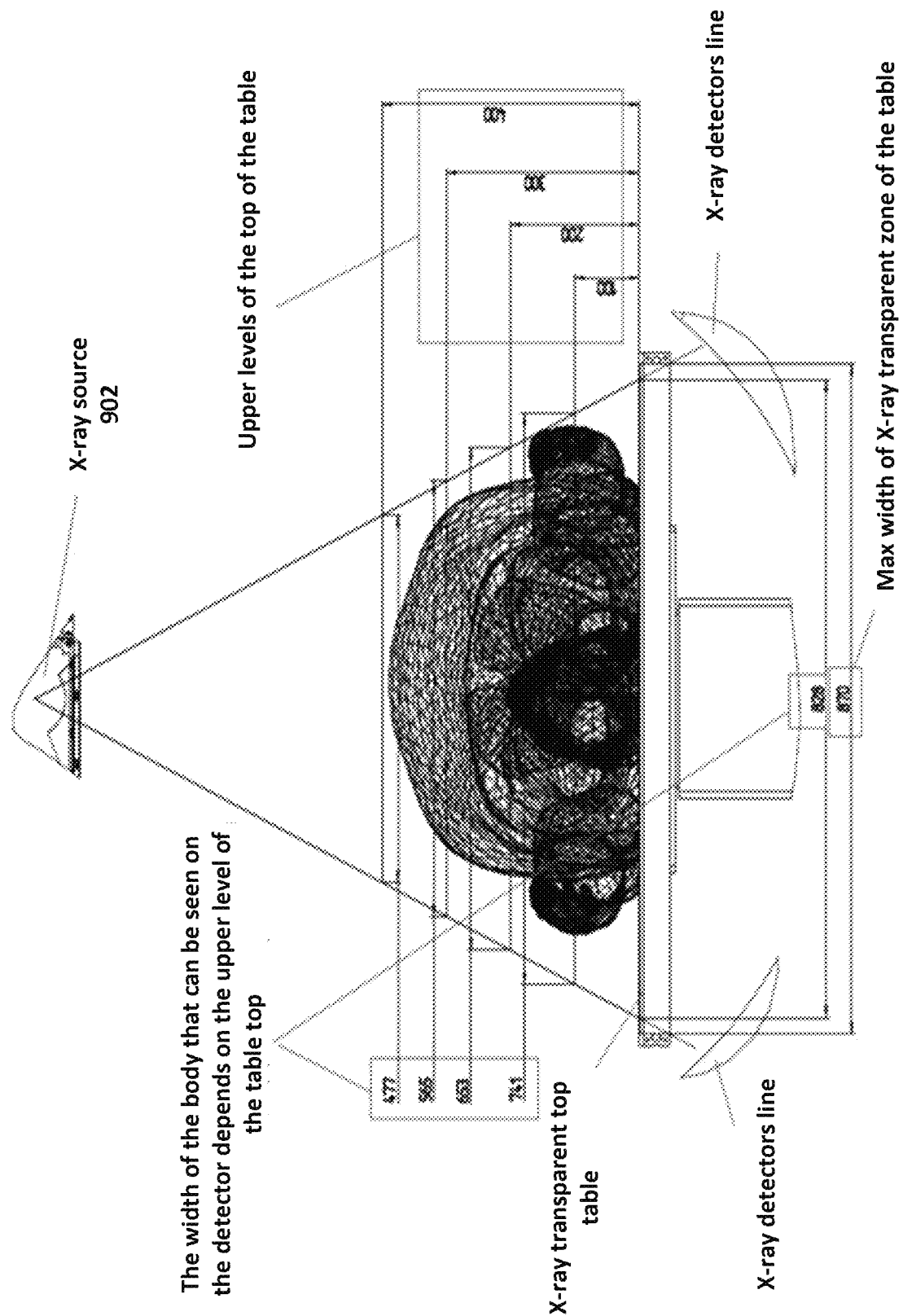
FIG. 9 is a view looking horizontally towards the head of the body
Figure 11B:
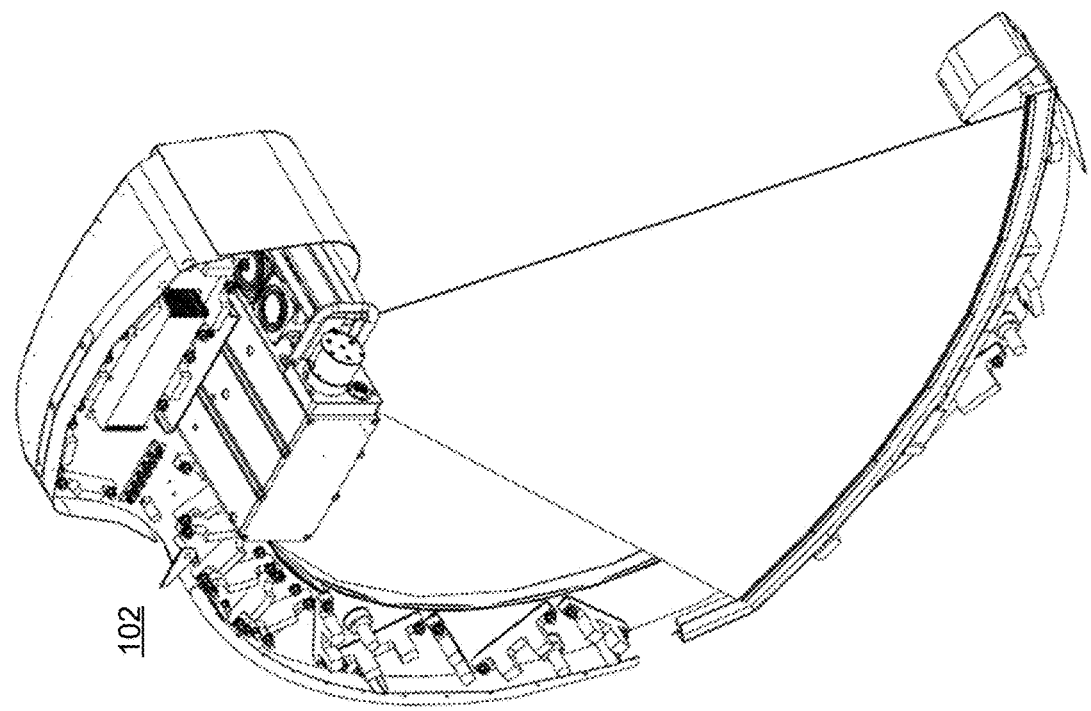
FIGS. 11A-11B is a perspective three-dimensional view of C-frame.
Figure 11A:
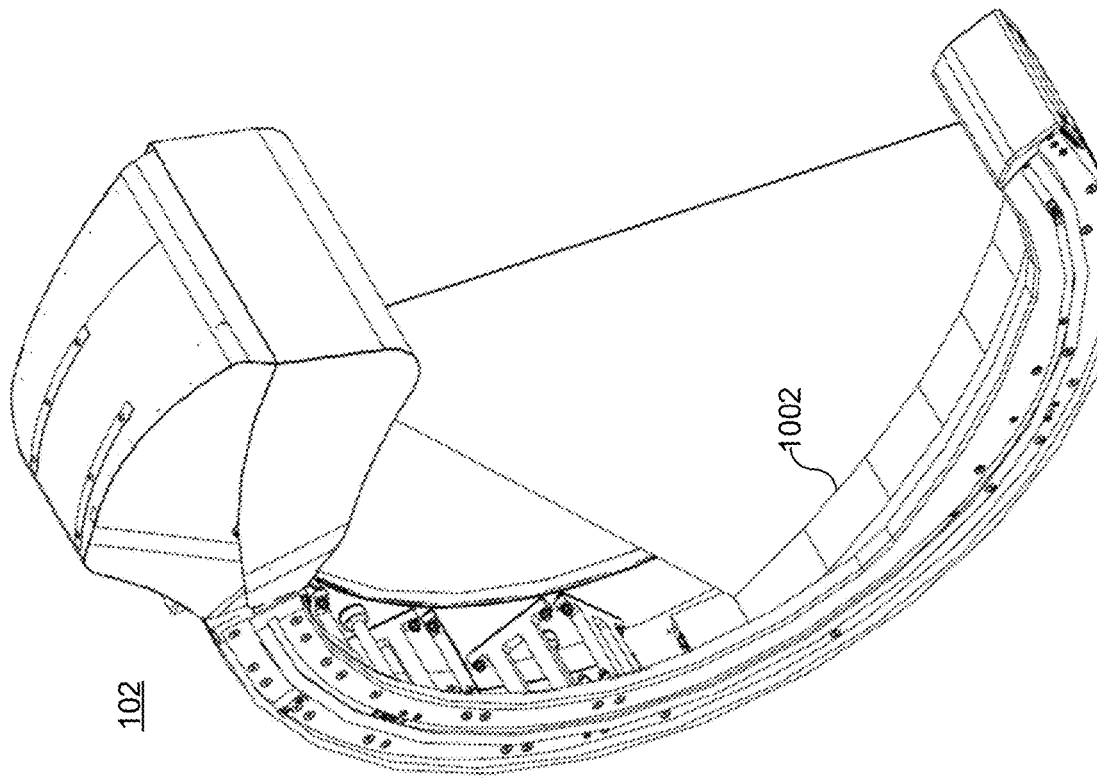
Figure 12A:
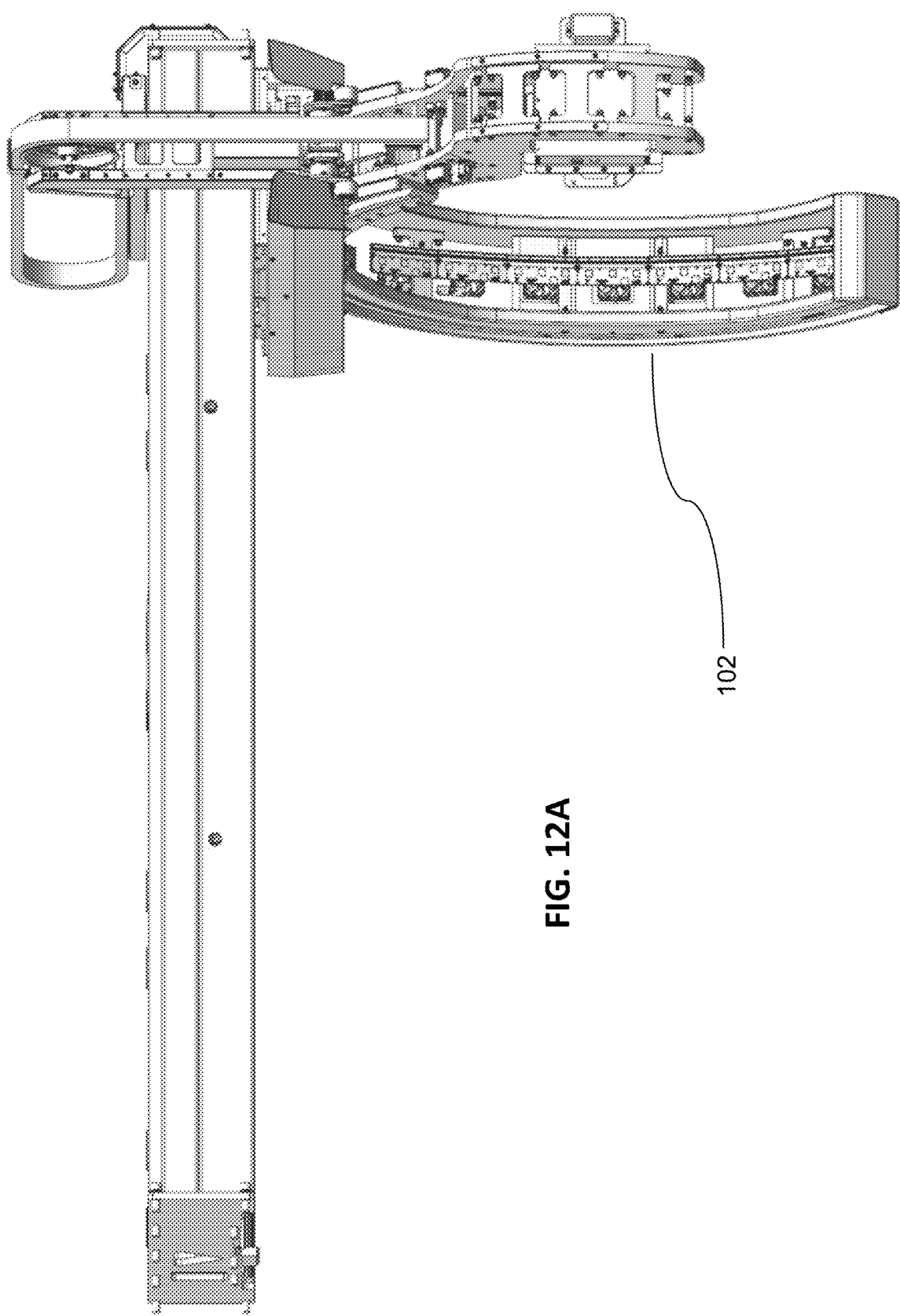
FIGS. 12A-12B show additional views of the C-frame and the detector arrays.
Figure 12B:
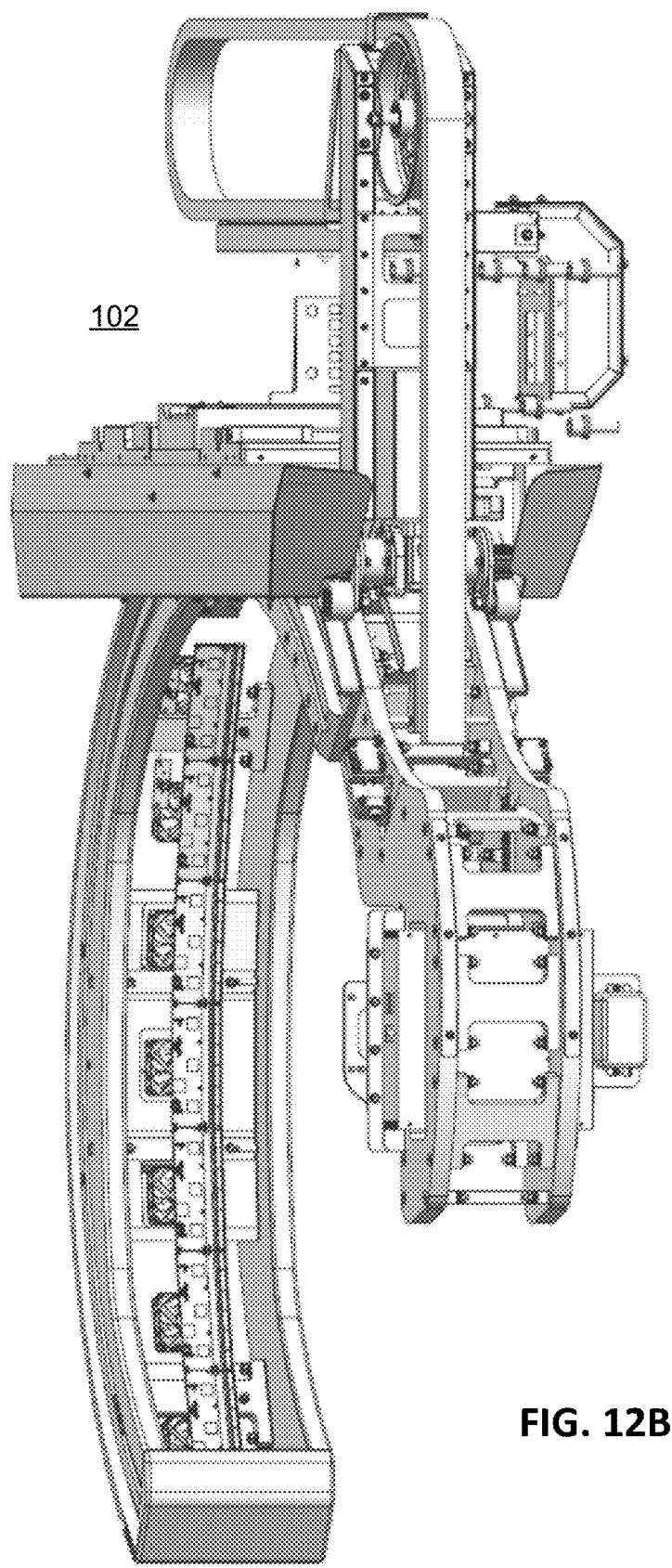

Given the large width of the table that is possible with the proposed arrangement of the detectors, a body up to 250 kg can be placed on the table and scanned (see FIG. 9, showing a view looking horizontally towards the head of the body, exemplary dimensions listed in mm). A larger scanning area (830×2100 mm) is also possible with the proposed arrangement, compared to conventional solutions.

The basic design of the scanner 100, shown in (FIG. 1-FIG. 5), can have various variants of the design while retaining its basic structural functionality, which allows to obtain high-contrast high-quality images.

The basic design can be modified in the X-ray protective design with sliding doors 1502 (see various perspective views shown in FIG. 15-FIG. 20), which allows to use the scanner without a special X-ray protective room.

Figure 21:
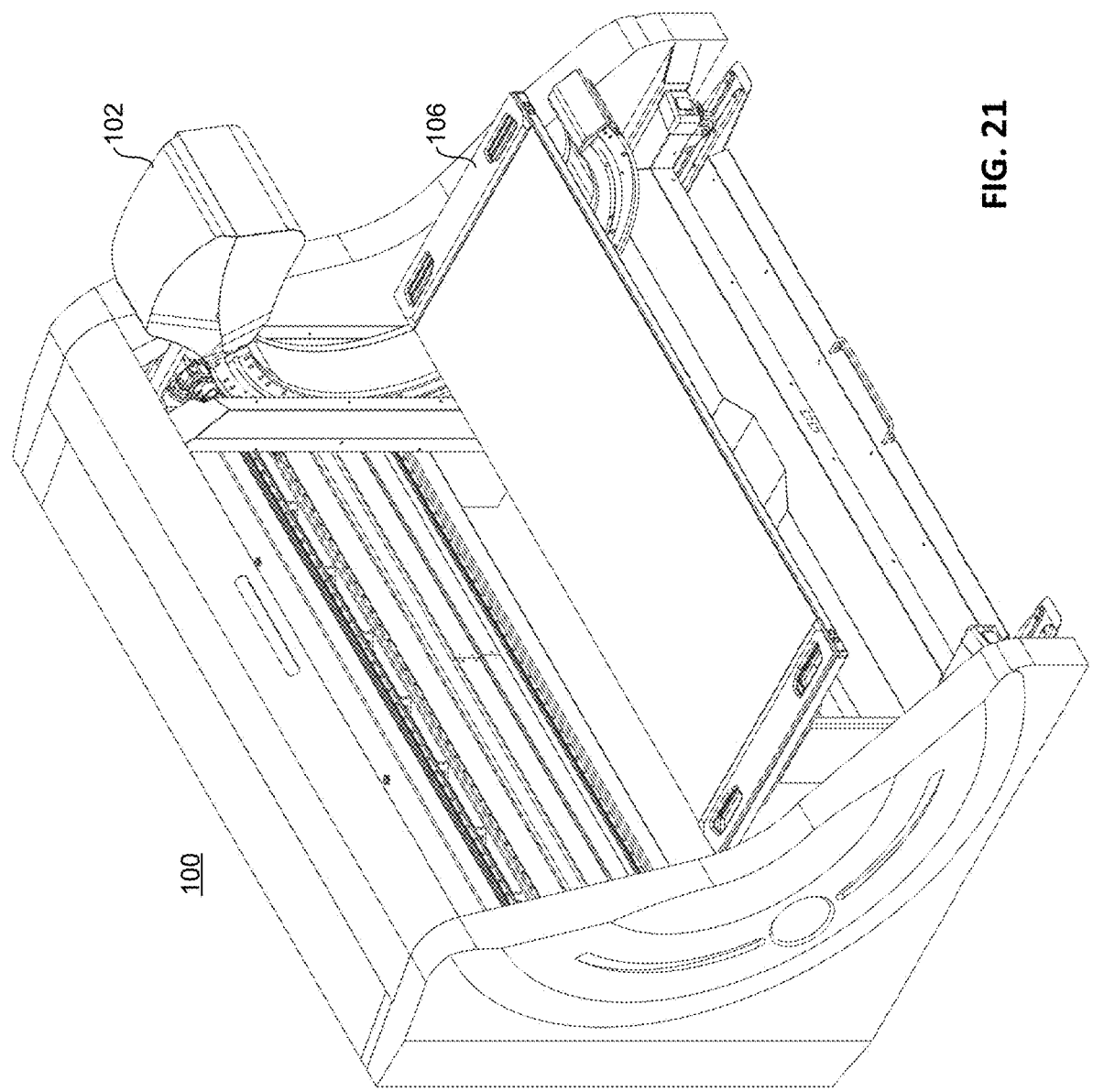
FIG. 21-FIG. 23 show perspective views of a variation of the design in a lightweight version.
Figure 22:
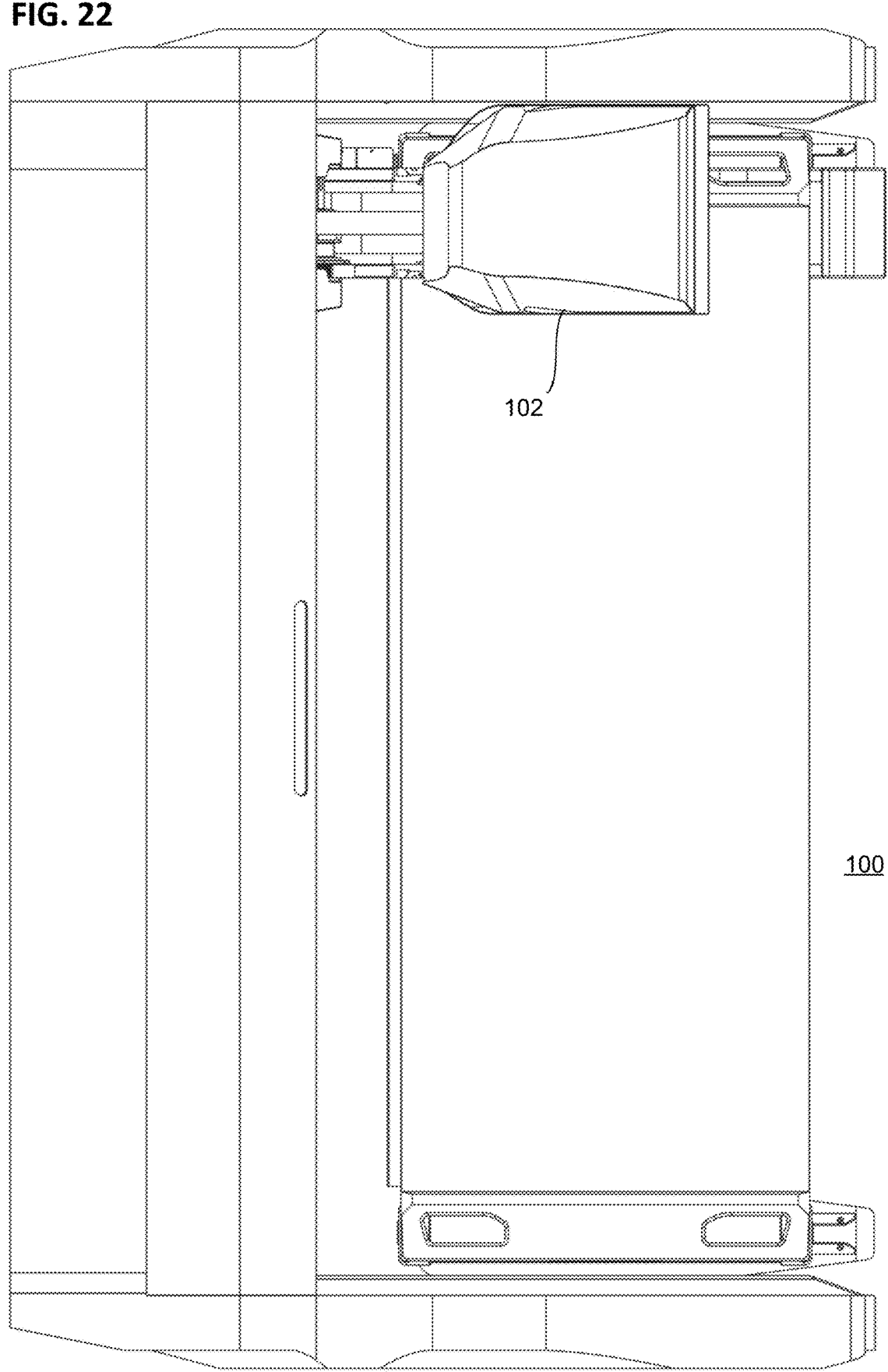
Figure 23:
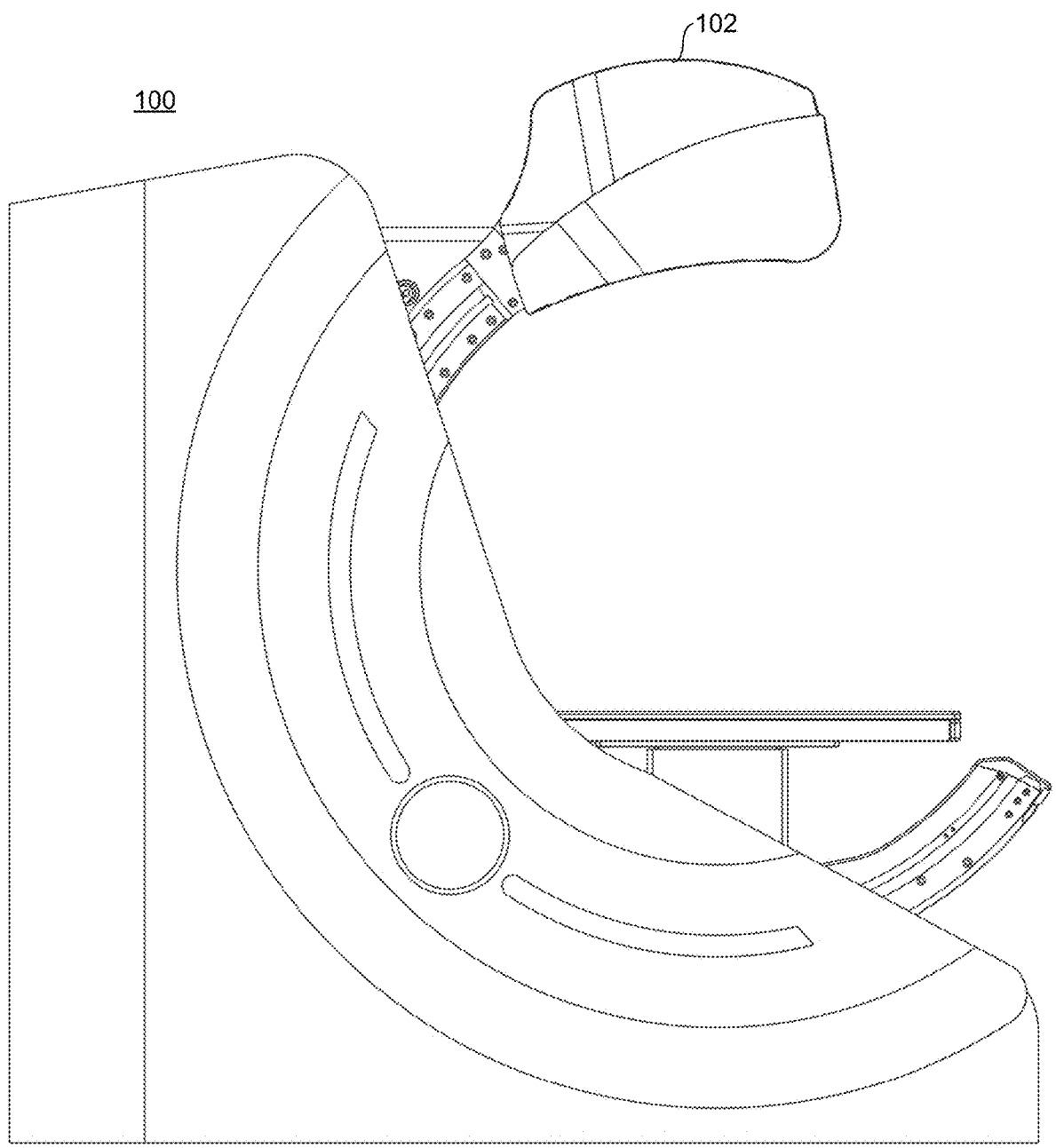

In the another version, the basic structure can be modified in the lightweight version (FIG. 21-FIG. 23), which allows to reduce its overall weight, dimensions and provide the visibility of the table with the patient and the scanning process from three sides. while maintaining the specified rigidity of the structure The direct photon counting detector can operate in a dual-energy mode. The advantage of using two energies in comparison with one is the ability to recognize different materials by atomic number (Z), which is achieved by comparing the degree of attenuation of x-rays for different energies, depending on the atomic number of the material.

For dual-energy technology, the estimate is based on the ratio between the low-energy (SE1) and high-energy (SE2) signals from the detector.

The ratio of the logarithms of the detector responses by the channels for low and high energies is unique for a given effective atomic number in a fairly wide range of atomic numbers of the elements contained in the identified material:

$$\frac{\ln(S_{E2})}{\ln(S_{E1})} = \eta(Z)$$

By recognizing the atomic numbers of the elements, it is possible to determine various organic and inorganic materials and with the use of the color palette to color them in different colors. This facilitates the process of detecting various foreign inorganic and organic inclusions in the patient's body under study.

As a further example, the proposed scanner for human bodies can be used for estimate the density of human bodies bones. That allows to diagnose osteoporosis before a broken bone occurs. This test helps to estimate the density of the bones and reduce the chance of breaking a bone.

Having thus described a preferred embodiment, it should be apparent to those skilled in the art that certain advantages of the described method and apparatus have been achieved.

It should also be appreciated that various modifications, adaptations, and alternative embodiments thereof may be made within the scope and spirit of the present invention. The invention is further defined by the following claims.

What is claimed is:

1. An X-ray imaging system comprising:
a frame;
a gantry mounted on the frame;
an electromagnetic linear drive coupled to the gantry for translating the gantry in a longitudinal horizontal direction for performing linear scanning of a human body;
a C-arm mounted on the gantry, the C-arm rotatable across at least a 90 degree angle;
an X-ray source mounted to one end of C-arm and having a focal spot;
an X-ray detector mounted to the opposite end of the C-arm,
the X-ray detector formed of a plurality of detector arrays arranged in an arc on the C-arm with adjacent detector arrays abutting each other, each detector array being a flat two-dimensional rectangular sensor,
each detector array of the plurality of detector arrays formed of a plurality of pixel lines,
each pixel line of the plurality of pixel lines is formed of a plurality of pixels,
wherein each detector array of the plurality of detector arrays is mounted perpendicular to a radial line between the focal spot of the X-ray source and a middle of each detector array.

2. The system of claim 1, wherein the pixels have a pixel size of 100 µm, and each detector array of the plurality of detector arrays has 64 pixel lines.

3. The system of claim 1, wherein each pixel line of the plurality of pixel lines is 153.6 mm long.

4. The system of claim 1, wherein the plurality of detector arrays includes 7 detector arrays, and wherein the 7 detector arrays are of a direct photon counting Cadmium Telluride type.

5. The system of claim 1, wherein an X-ray transparent width of a table that can be positioned within the C-arm, with a body to be scanned thereon with the linear scanning, is 830 mm.

6. The system of claim 1, wherein the system forms a two-dimensional image of the human body being scanned by combining images formed by the X-ray detector as the C-arm is being translated in the longitudinal horizontal direction in a single scan.

7. The system of claim 6, wherein the image is generated in a TDS (Time Delayed Summation) mode.

8. The system of claim 1, wherein the X-ray source has a maximum current of 2.5 mA and a maximum voltage of 200 kV.

9. The system of claim 1, wherein the X-ray source has a focal spot of 0.8 mm and a fan angle of 49.7°.

10. The system of claim 1, wherein the X-ray detector is used to identify organic and inorganic materials using a direct photon counting detector.

11. The system of claim 1, wherein the X-ray detector is used to estimate bone density throughout the entire human body in a single scan.

12. The system of claim 1, wherein the frame forms an enclosure with doors.

13. The system of claim 1, wherein an active width of each detector array of the plurality of detector arrays is 6.4 mm.

14. The system of claim 1, wherein each pixel of the plurality of pixels have a pixel size of 100 µm.

15. The system of claim 1, wherein a distance from a focal point of the X-ray source to a center of each detector array of the plurality of detector arrays is 1237.6 mm.

16. An X-ray imaging system comprising:
a frame;
a gantry mounted on the frame;
an electromagnetic drive coupled to the gantry for translating the gantry in a longitudinal direction for performing linear scanning of a human body;
a C-arm mounted on the gantry, the C-arm rotatable across at least a 90 degree angle;
an X-ray source mounted to one end of C-arm and having a focal spot;
an X-ray detector mounted to the opposite end of the C-arm,
the X-ray detector including a plurality of flat two-dimensional rectangular detector arrays arranged in an arc on the C-arm,
each detector array of the plurality of detector arrays formed of a plurality of pixel lines,
each pixel line of the plurality of pixel lines formed of a plurality of pixels,
wherein each detector array of the plurality of detector arrays is mounted perpendicular to a radial line between the focal spot of the X-ray source and a middle of each detector array, and
wherein the plurality of detector arrays includes 7 detector arrays.

17. The system of claim 16, wherein the system forms a two-dimensional image of the human body being scanned by combining images formed by the X-ray detector as the C-arm is being translated in the longitudinal direction in a single scan.

18. The system of claim 16, wherein an active width of each detector array of the plurality of detector arrays is 6.4 mm.

19. The system of claim 1, wherein each pixel of the plurality of pixels have a pixel size of 100 µm.

* * * * *